(12) United States Patent
Cohen

(10) Patent No.: US 7,927,580 B2
(45) Date of Patent: Apr. 19, 2011

(54) TAT-BASED IMMUNOMODULATORY COMPOSITIONS AND METHODS OF THEIR DISCOVERY AND USE

(75) Inventor: David I. Cohen, Pelham, NY (US)

(73) Assignee: NaniRx, Inc., New York, NY (US)

( * ) Notice: Subject to any disclaimer, the term of this patent is extended or adjusted under 35 U.S.C. 154(b) by 478 days.

(21) Appl. No.: 10/598,978

(22) PCT Filed: Mar. 16, 2005

(86) PCT No.: PCT/US2005/008694
§ 371 (c)(1),
(2), (4) Date: Sep. 15, 2006

(87) PCT Pub. No.: WO2005/090968
PCT Pub. Date: Sep. 29, 2005

(65) Prior Publication Data
US 2008/0155703 A1    Jun. 26, 2008

Related U.S. Application Data

(60) Provisional application No. 60/553,733, filed on Mar. 16, 2004.

(51) Int. Cl.
*A61K 49/00* (2006.01)
*C12Q 1/70* (2006.01)
*C12Q 1/02* (2006.01)
*G01N 33/543* (2006.01)
*G01N 33/566* (2006.01)

(52) U.S. Cl. ............... 424/9.2; 435/5; 435/29; 436/501; 436/518

(58) Field of Classification Search .................. None
See application file for complete search history.

(56) References Cited

U.S. PATENT DOCUMENTS

| | | |
|---|---|---|
| 5,585,103 A | 12/1996 | Raychaundhuri et al. |
| 5,597,895 A | 1/1997 | Gaynor et al. |
| 5,616,559 A | 4/1997 | Androphy et al. |
| 5,652,122 A | 7/1997 | Frankel et al. |
| 5,656,599 A | 8/1997 | Androphy et al. |
| 5,670,617 A | 9/1997 | Frankel et al. |

(Continued)

FOREIGN PATENT DOCUMENTS

EP        0 673 948        11/1998

(Continued)

OTHER PUBLICATIONS

Darbinian, et al. Functional interaction between cyclin T1rcdk9 and Pura determines the level of TNFa promoter activation by Tat in glial cells. Journal of Neuroimmunology 121Ž2001.3-11.*

(Continued)

*Primary Examiner* — Mary E Mosher
*Assistant Examiner* — Stuart W Snyder
(74) *Attorney, Agent, or Firm* — K&L Gates LLP; Louis C. Cullman; Michelle Glasky Bergman

(57) ABSTRACT

A method for identifying new immunomodulatory chemical entities (NICE) comprising reacting a candidate NICE with a Tat SH3 binding domain, identifying the bound candidate NICE and determining whether the candidate NICE induces monocytes to differentiate into dendritic cells (DC) or regulatory macrophages (AReg). In particular, the present invention relates to identifying NICE that are either immunostimulatory or immunosuppressive.

5 Claims, 13 Drawing Sheets

U.S. PATENT DOCUMENTS

| | | | |
|---|---|---|---|
| 5,674,980 | A | 10/1997 | Frankel et al. |
| 5,686,264 | A | 11/1997 | Gaynor et al. |
| 5,747,641 | A | 5/1998 | Frankel et al. |
| 5,804,604 | A | 9/1998 | Frankel et al. |
| 5,889,175 | A | 3/1999 | Mehtali et al. |
| 5,891,994 | A | 4/1999 | Goldstein |
| 5,942,401 | A | 8/1999 | van Baalen et al. |
| 5,981,258 | A | 11/1999 | Mehtali et al. |
| 6,024,965 | A | 2/2000 | van Baalen et al. |
| 6,132,721 | A | 10/2000 | Zagury et al. |
| 6,193,981 | B1 | 2/2001 | Goldstein |
| 6,194,388 | B1 | 2/2001 | Krieg et al. |
| 6,200,575 | B1 | 3/2001 | Zagury et al. |
| 6,207,646 | B1 | 3/2001 | Krieg et al. |
| 6,228,369 | B1 | 5/2001 | Mehtali et al. |
| 6,239,116 | B1 | 5/2001 | Krieg et al. |
| 6,270,769 | B1 | 8/2001 | Raychaudhuri et al. |
| 6,284,252 | B1 | 9/2001 | Mehtali et al. |
| 6,316,003 | B1 | 11/2001 | Frankel et al. |
| 6,319,666 | B1 | 11/2001 | van Baalen et al. |
| 6,339,068 | B1 | 1/2002 | Krieg et al. |
| 6,406,705 | B1 | 6/2002 | Davis et al. |
| 6,420,141 | B1 | 7/2002 | Zagury et al. |
| 6,495,347 | B1 | 12/2002 | Siegel et al. |
| 6,497,880 | B1 | 12/2002 | Wisniewski |
| 6,524,582 | B2 | 2/2003 | Goldstein |
| 6,524,825 | B1 | 2/2003 | Mizzen et al. |
| 6,525,179 | B1 | 2/2003 | Goldstein |
| 6,593,292 | B1 | 7/2003 | Rothbard et al. |
| 6,657,055 | B2 | 12/2003 | Siegel et al. |
| 6,667,151 | B1 * | 12/2003 | Cohen .............................. 435/5 |
| 6,686,333 | B1 | 2/2004 | Kashanchi et al. |
| 6,797,491 | B2 | 9/2004 | Neefe et al. |
| 2002/0091073 | A1 | 7/2002 | Finkel et al. |
| 2002/0193330 | A1 | 12/2002 | Hone |
| 2002/0197269 | A1 | 12/2002 | Lingnau et al. |
| 2003/0003106 | A1 | 1/2003 | Zagury et al. |
| 2003/0091599 | A1 | 5/2003 | Davis et al. |
| 2003/0099663 | A1 | 5/2003 | Fleitmann et al. |
| 2003/0099664 | A1 | 5/2003 | Wisniewski |
| 2003/0148456 | A1 | 8/2003 | Mizzen et al. |
| 2003/0158134 | A1 | 8/2003 | Voss |
| 2003/0162719 | A1 | 8/2003 | Rothbard et al. |
| 2003/0166832 | A1 | 9/2003 | Goldstein |
| 2003/0180326 | A1 | 9/2003 | Goldstein |
| 2003/0224010 | A1 | 12/2003 | Davis et al. |
| 2003/0232074 | A1 | 12/2003 | Lipford et al. |
| 2004/0001852 | A1 | 1/2004 | Zagury et al. |
| 2004/0005330 | A1 | 1/2004 | Rappaport et al. |
| 2004/0009949 | A1 | 1/2004 | Krieg |
| 2004/0028652 | A1 | 2/2004 | Wang et al. |
| 2004/0034209 | A1 | 2/2004 | Ho et al. |
| 2004/0054137 | A1 | 3/2004 | Thomson et al. |

FOREIGN PATENT DOCUMENTS

| | | |
|---|---|---|
| EP | 0 814 834 | 9/2000 |
| EP | 1 279 404 | 1/2003 |
| WO | 91/15224 | 10/1991 |
| WO | 91/18454 | 11/1991 |
| WO | 94/15634 | 7/1994 |
| WO | 95/31999 | 11/1995 |
| WO | 96/27389 | 9/1996 |
| WO | 98/14589 | 4/1998 |
| WO | 98/17309 | 4/1998 |
| WO | 98/43669 | 10/1998 |
| WO | 98/46083 | 10/1998 |
| WO | 99/02185 | 1/1999 |
| WO | 99/16884 | 4/1999 |
| WO | 99/27958 | 6/1999 |
| WO | 99/33346 | 7/1999 |
| WO | 99/33872 | 7/1999 |
| WO | 00/03732 | 1/2000 |
| WO | 00/78334 | 12/2000 |
| WO | 00/78969 | 12/2000 |
| WO | 01/00232 | 1/2001 |
| WO | 01/24822 | 4/2001 |
| WO | 01/43771 | 6/2001 |
| WO | 01/78775 | 10/2001 |

OTHER PUBLICATIONS

Cohen, et al. "Pronounced acute immunosuppression in vivo mediated by HIV Tat challenge" Proceedings of the National Academy of Sciences of the United States of America. 1999; 96(19):10842-10847.*

Cheadle, et al. "Identification of a Src SH3 domain binding motif by screening a random phage display library" Journal of Biological Chemistry. 1994; 269(39):24034-24039.*

Bagh Ian, et al. "Protective immunity against lethal HSV-1 challenge in mice by nucleic acid-based im munisation with herpes simplex virus type-I genes specifying glycoproteins gB and gD" Journal of Medical Microbiology. 2002; 51(4): 350-357.*

Agwale SM et al. A Tat subunit vaccine confers protective immunity against the immunemodulating activity of the human immunodeficiency vir type1 Tat protein in mice PNAS 99:1003710041 2002.

Arlen PM. et al. Strategies for the Development of PSAbased vaccines for the treatment of advanced prostate cancer Expert Rev. Vaccines vol. 2 No. 4 pp. 483493 2003.

Badley AD. et al. Upregulation of Fas Ligand Expression by Human Immunodeficiency Vir in Human Macrophages Mediates Apoptosis of Uninfected T Lymphocytes J Virol 70:199206 Jan. 1996.

Badley AD. et al. Macrophagedependent Apoptosis of CD4+ T Lymphocytes from HIVinfected Individuals is Mediated by FasL and Tumor Necrosis Factor J. Exp. Med. vol. 185 No. 1 pp. 5564 Jan. 6, 1997.

Baghian, A. et al., "Protective immunity against lethal HSV-1 challenge in mice by nucleic acid-based immunization with herpes simplex virus type-1 genes specifying glycoproteins gB and gD", Journal of Medical Microbiology, vol. 51, No. 4, 2002, pp. 350-357.

Banchereau J et al. Dendritic cells as vectors for therapy Cell 106:2714 2001.

Bayer P et al. Structural Studies of HIV1 Tat Protein J. Mol. Biol. vol. 247 pp. 529535 1995.

Beissert S. et al. IL10 Inhibits Tumor Antigen Presentation by Epidermal AntigenPresenting Cells The Journal of Immunology vol. 154 pp. 12801286 1995.

Buanec HL et al. A prophylactic and therapeutic AIDS vaccine containing as a component the innocuo Tat Toxoid Biomedicine and Pharmacotherapy Vo. 52 No. 10 pp. 431435 1998.

Boykins, R.A., et al., "Immunication with a noval HIV-1-Tat multiple-peptide conjugate induces effective immune response in mice", Peptides, 2000, vol. 21, , pp. 1829-1847.

Cafaro A. et al. Control of SHIV89.6Pinfection of cynomolg monkeys by HIV1 Tat protein vaccine Nature Medicine vol. 5 No. 6 pp. 643650 Jun. 1999.

Caputo A. et al. Immunization with low doses of HIV1 tat DNA delivered by novel cationic block copolymers induces CTL responses against Tat Vaccine vol. 21 pp. 11031111 2003.

Caselli E. et al. DNA immunization with HIV1 tat mutated in the trans activation domain induces humoral and cellular immune responses against wildtype Tat. J Immunol 162:56318 1999.

Cheadle, C., et al., :"Identification of a Src SH3 Domain Binding Motif by Screening a Random Phage Display Library", The Journal of Biological Chemistry, 1994, vol. 269, No. 39, pp. 24034-24039.

Chenciner et al. Enhancement of humoral immunity to SIVenv following simultaneo inoculation of mice by three recombinant adenovires encoding SIVenvpoliovir chimeras Tat and Rev. AIDS Res Hum Retrovires 13:8016 1997.

Cho H. et al. In vitro induction of carcioembryonic antigen (CEA)specific cytotoxic T lymphocytes by dendritic cells transduced with recombinant adenovires Vaccine vol. 22 pp. 224236 2003.

CNN Interactive New HIV Vaccine Concept May Extend Hope to Those Already Infected htt:cnn.comHEALTHaids990829aids.vaccine. pp. Aug. 13, 1999.

Cohen SS et al. Pronounced acute immunosuppression in vivo mediated by HIV1 Tat challenge Proc Natl Acad Sci A 96:1084247 1999.

Dalyotherman N et al. Reversal of CD8+ T cell ignorance and induction of antitumor immunity by peptidepulsed APC J Immunol 165:67317 2000.

Durrant LG et al. Cancer vaccines entering Phase III clinical trials Expert Opinion Emerging Drugs vol. 8 No. 2 pp. 489500 2003.

Elbashir SM et al. RNA Interference is mediated by 21 and 22nucleotide RNAs. Genes Devel 15:188200 2001.

Embury, J., et al., Proteins Linked to a Protein Transduction Domain Efficiently Transduce Pancreatic Islets:, Diabetes, 2001, vol. 50, pp. 1706-1713.

Ensoli, B., et al., "HIV-1 Tat vaccines, Virus Research", 2002 vol. 82, pp. 91-101.

Fanalesbelasio E et al. Native HIV1 Tat protein targets monocytederived dendritic cells and enhances their maturation function and antigenspecific T cell responses J Immunol 168:197206 2002.

Fanalesbelasio E. et al. HIV1 TatBased Vaccines: From Basic Science to Clinical Trials DNA & Cell Biology vol. 21 No. 9 pp. 599610 2002.

Fawell, S., et al., Tat-mediated delivery of heterologuous proteins into cells, Proc. Natl. Acad. Sci., 1994, vol. 91, pp. 664-668.

Fisher GH. et al. Dominant Interfering Fas Gene Mutations Impair Apoptosis in a Human Autoimmune Lymphoproliferative Syndrome Cell vol. 81 pp. 935946 Jun. 16 1995.

Follen M et al. Cervical Cancer Chemoprevention Vaccines and Surrogate Endpoint Biomarkers American Cancer Society Cancer Supplement vol. 98 No. 9 pp. 20442051 Nov. 1, 2003.

Frankel AD and Pabo Co Cellular uptake of the Tat protein from Human Immunodeficiency Vir Cell 55:118993 1988.

Frankel AD et al. Activity of synthetic peptides from the TAT protein of human immunodeficiency vir type 1 Proc. Natl. Acad. Sci. vol. 86 pp. 73977401 Oct. 1989.

Friedman AD et al. Expression of a truncated viral transactivator selectively impedes lytic infection by its cognate vir Nature vol. 335 pp. 452454 Sep. 29, 1988.

Gallo RC. Tat as one key HIVinduced immune pathogenesis and Tat toxoid as an important component of a vaccine Proc. Natl. Acad. Sci. A vol. 96 pp. 83248326 Jul. 1999.

Garciahernandez ML et al. Interleukin10 promotes B16melanoma growth by inhibition of macrophage functions and induction of tumour and vascular cell proliferation Immunology vol. 105 pp. 231243 2002.

Giannouli C. et al. Fion of a Tumourassociated Antigen to HIV1 Tat Improves Proteinbased Immunotherapy of Cancer Anticancer Research vol. 23 pp. 35233532 2003.

Goldstein G. HIV1 Tat protein as a potential AIDS vaccine Nature Medicine vol. 1 No. 9 pp. 960964 Sep. 1996.

Green M et al. Mutational Analysis of HIV1 Tat Minimal Domain Peptides: Identification of TransDominant Mutants that Suppress HIVLTRDriven Gene Expression Cell vol. 58 pp. 215223 Jul. 14, 1989.

Gringeri A. et al. Safety and Immunogenicity of HIV1 Tat Toxoid in Immunocompromised HIV1Infected Patients Journal of Human Virology vol. 1, No. 4 pp. 293298 May/Jun. 1998.

Gringeri A. et al. Tat Toxoid as a Component of a Preventive Vaccine in Seronegative Subjects Journal of Acquired Immune Deficiency Syndromes and Human Retrovirology vol. 20 No. 4 pp. 371375 Apr. 1, 1999.

Hernando JJ et al. Dendritic Cellbased Vaccines in Breast and Gynaecologic Cancer Anticancer Res. 23:42934304 2003.

Hsieh CL et al. TumorInduced Immunosupression: A Barrier to Immunotherapy of Large Tumors by CytokineSecreting Tumor Vaccine Human Gene Therapy vol. 11 pp. 681692 Mar. 20, 2000.

Ishigami S. et al. Tumorassociated Macrophage (TAM) Infiltration in Gastric Cancer Anticancer Research vol. 23 pp. 40794084 2003.

Jager D. et al. Identification of tumor antigens as potential target antigens for immunotherapy by serological expression cloning htt:www.springerlink.commediagmgkwgmxxeebf3wn9h2mContributinsX39FX39 pp. 19 2004.

Jasinska J. et al. Inhibition of Tumor Cell Growth by Antibodies Induced After Vaccination with Peptides Derived From the Extracellular Domain of Her2NEU Int. J. Cancer vol. 107 pp. 976983 2003.

Jiang S. et al. Fas Mediates Apoptosis and OxidantInduced Cell Death in Cultured hRPE Cells Invest Ophthalmol Vis Sci. vol. 41 No. 3 pp. 645655 2000.

Kanazawa M. et al. Effect of DC Therapy Combined with Chemotherapy in Advanced Cancer Cases Jpn J. Cancer Chemother vol. 30 No. 11 pp. 16551660 Oct. 2003.

Kjaergaard J. et al. Electrofion of syngeneic dendritic cells and tumor generates potent therapeutic vaccine Cellular Immunology vol. 225 pp. 6574 2003.

Kuppwamy M. et al. Multiple functional domains of Tat the transactivator of HIV1 defined by mutational analysis Nucleic Acids Research vol. 17 No. 9 pp. 35513561 1989.

Leonard NJ et al. Periodate Oxidation of Sulfides to Sulfoxides. Scope of the Reaction The Journal of Organic Chemistry vol. 27 No. 1 pp. 282284 Jan. 1962.

Lepplewienhues A. et al. Stimulation of CD95 (Fas) blocks T lymphocyte calcium channels through sphingomyelinase and sphingolipds PNAS vol. 96 No. 24 pp. 1379513800 Nov. 23, 1999.

Lewis SN Peracid and Peroxidase Oxidation. In: Oxidation: Techniques and Applications in Organic Synthesis vol. 1 R.L. Augtine ed. Marcel Dekker Inc. New York pp. 244248 1969.

Li CJ et al. Tat protein induces selfperpetuating permissivity for productive HIV1 infection Proc. Natl. Acad. Sci A vol. 94 pp. 81168120 Jul. 1997.

Li CJ. et al. Induction of Apoptosis in Uninfected Lymphocytes by HIV1 Tat Protein Science vol. 268 pp. 429431 Apr. 21, 1995.

Lin EY et al. The Macrophage Growth Factor CSF1 in Mammary Gland Development and Tumor Progression Journal of Mammary Gland Biology and Neoplasia vol. 7 No. 2 pp. 147162 Apr. 2002.

Liu KJ et al. Concurrent delivery of tumor antigens an activation signals to dendritic cells by irradiated CD40 ligandtransfected tumor cells resulted in efficient activation of specific CD8+ T cells Cancer Gene Therapy vol. 11 pp. 135147 2004.

Martin MJ et al. Human embryonic stem cells express an immunogenic nonhuman sialic acid. Nat Med 11:22832 2005.

Medina F. et al. Regulatory role of CD95 ligation on human B Cells induced in vivo capable of spontaneo and highrate Ig secretion Eur. J. Immunol. vol. 27 pp. 700706 1997.

Moy P et al. Tatmediated protein delivery can facilitate MHC class I presentation of antigens Mol Biotechnol 6:10513 1996.

Nagata S. Apoptosis by Death Factor Cell vol. 88 pp. 355365 Feb. 7, 1997.

Nourishirazi M. et al. Dendritic cell based tumor vaccines Immunology Letters vol. 74 pp. 510 2000.

Novak N. et al. Engagement of FcεRI on human monocytes induces the production of IL10 and prevents their differentiation in dendritic cells J Immunol 167:797804 2001.

Paillard F. Immonosupression Mediated by Tumor Cells: A Challenge for Immunotherapeutic Approaches Human Gene Therapy vol. 11 pp. 657658 Mar. 20, 2000.

Peter ME et al. Resistance of cultured peripheral T cells towards activationinduced cell death involves a lack of recruitment of FLICE (machCASPASE 8) to the CD95 deathinducing signaling complex Eur. J. Immunol. vol. 27 pp. 12071212 1997.

Phan CQ et al. Cancer regression and autoimmunity induced by cytotoxic T lymphocyteassociated antigen 4 blockade in patients with metastatic melanoma Proc Natl Acad Sc. A 100:83727 2003.

Rana TM et al. Biochemical and Functional Interactions between HIV1 Tat Protein and TAR RNA Archives of Biochemistry and Biophysics vol. 365 No. 2 pp. 175185 May 15, 1999.

Reinhold D. et al., "HIV-1 Tat: Immunosupression via TGF-betal Induction", Immunology Today, Elsevier Pubications, vol. 20, No. 8, 1999, p. 384.

Schluesener HJ Protection against generalized autoimmunity of the nervo system (GANS) a novel animal model with combined features of EAE EAN and EAU by a recombinant HIV1 Tat3772 peptidebased multiple T cell epitope vaccine. FEMS Immunol Med Microbiol 17:17986 1997.

Schluesener HJ Protection against experimental nervo system autoimmune diseases by a human immunodeficiency virl Tat peptidebased polyvalent vaccine. J Neurosci Res. 46:25862 1996.

Schwarze SR et al. In vivo protein transduction: delivery of a biologically active protein into the moe Science 285:156972 1999.

Small EJ et al. Immunotherapy of HormoneRefractory Prostate Cancer with AntigenLoaded Dendritic Cells Journal of Clinical Oncology vol. 18 No. 23 pp. 38943903 Dec. 1, 2000.

Stebbing J et al. Diseaseassociated dendritic cells respond to diseasespecific antigens through the common heal shock protein receptor Blood 102:180814 2003.

Stohl W. et al. Promotion of Activated Human B Cell Apoptosis and Inhibition of Ig Production by Soluble CD95 Ligand: CD95Based Downregulation of Ig Production Need Not Culminate in Activated B Cell Death Cellular Immunology vol. 203 pp. 111 2000.

Stohl W. et al. SuperantigenDriven CD8+ T CellMediated DownRegulation: CD95 (Fas)Dependent DownRegulation of Human Ig Responses Despite CD95Independent Killing of Activated B Cells The Journal of Immunology vol. 161 pp. 32923298 1998.

Suzue K et al. Heat shock fion proteins as vehicles for antigen delivery into the major histocompatibility complex class I presentation pathway Immunol 94:1314651 1997.

Tasca, S., et al., "Escape of monocyte-derived dentritic cells of HIV-1 inected individuals from natural killer cell0mediated lysis" AIDS, vol. 17, No. 16, 2003, pp. 2291-2298.

Tosi G et al. Highly stable oligomerization forms of HIV1 Tat detected by monoclonal antibodies and requirement of monomeric forms for the transactivating function on the HIV1 LTR Eur J Immunol 30:11206 2000.

Turtle CJ et al. Dendritic Cells in Tumor Immunology and Immunotherapy Current Drug Targets vol. 5 No. 1 pp. 1739 2004.

Tzachanis D et al. Blockade of B7CD28 in mixed lymphocyte reaction cultures results in the generation of alternatively activated macrophages which suppress Tcell responses Blood 99:146573 2002.

Viscidi RP et al Inhibition of antigeninduced lymphocyte proliferation by Tat protein from HIV1 Science 146:16068 1989.

Visscher DW et al. Clinicopathologic Analysis of Macrophage Infiltrates in Breast Carcinoma Path. Res. Pract (Suppl). vol. 191 pp. 11331139 1995.

Vocero-Akbani, A.M. et al., "Killing HIV-Infected Cells by Transduction with an HIV Protease-Activated Caspase-3 Protein", Nature Medicine, vol. 5, No. 1, pp. 29-33, 1999.

Von Bernstorff W. et al. Systemic and Local Immunosupression in Pancreatic Cancer Patients Clinical Cancer Research vol. 7 pp. 925s932s Mar. 2001.

Wachsman W. et al. HTLV x Gene Mutants Exhibit Novel Transcriptional Regulatory Phenotypes Science vol. 235 pp. 674677 Feb. 6, 1987.

Westendrop MO. et al. Sensitization of T Cells to CD95mediated apoptosis by HIV1 Tat and gp120 Nature vol. 375 pp. 497500 Jun. 8, 1995.

Zhang H et al. Induction of specific T cell tolerance by Fas ligandexpressing antigenpresenting cells J Immunol 162:142330 1999.

* cited by examiner

Days Post Tumor Implant

Days Post Tumor Implant

TAT-BASED IMMUNOMODULATORY COMPOSITIONS AND METHODS OF THEIR DISCOVERY AND USE

RELATED APPLICATIONS

The present application claims priority to U.S. Provisional Patent Application Ser. No. 60/553,733 filed Mar. 16, 2004.

FIELD OF THE INVENTION

The present invention relates to the field of immune modulation therapeutics and more specifically to new Tat-based immunomodulatory chemical entities (NICE) useful in suppressing inappropriate immune responses in autoimmune diseases and organ transplantation and stimulating immune responses for the therapy of cancer and infectious diseases. Specifically, the NICE compositions of the present invention are can duplicate the immunosuppressive activities of the human immunodeficiency virus (HIV) trans-activator of transcription (Tat) and the immunostimulatory activities of Tat variants.

BACKGROUND OF THE INVENTION

Recently, significant advances have been made in understanding the human immunodeficiency disease (HIV) process. For many years, researchers have been unable to explain the seemingly immediate and profound destruction of the immune system following the initial HIV infection. Equally puzzling was a phenomenon seen in a few patients referred to as long term non-progessors (LTNP). In LTNP patients, viral loads are high and the virus can be isolated easily from the HIV target immune cells such as CD4+T lymphocytes (referred to herein as T4 cells). However, unlike the majority of infected individuals who develop acquired immune deficiency syndrome (AIDS), the LTNP do not demonstrate significant reduction in their T4 cells and do not progress to AIDS.

One possible, non-binding, theory that may explain these two phenomena involves a non-structural protein (a protein encoded by the virus genome that is not actually part of the virus itself) called the trans-activator of transcription (Tat). Tat is a variable RNA binding peptide of 86 to 110 amino acids in length that is encoded on two separate exons of the HIV genome. Tat is highly conserved among all human lentiviruses and is essential for viral replication. When lentivirus Tat binds to the TAR (trans-activation responsive) RNA region, transcription (conversion of viral RNA to DNA then to messenger RNA) levels increase significantly. The Tat protein associated with lentivirus virulence will be referred to hereinafter as Tat, Recently, it has been demonstrated that Tat increases viral RNA transcription and it has been proposed that Tat may initiate apoptosis (programmed cell death) in T4 cells and macrophages (a key part of the body's immune surveillance system for HIV infection) and possibly stimulates the over production of alpha interferon ($\alpha$-interferon is a well established immunosuppressive cytokine). These, and other properties of lentivirus Tat proteins, have led to considerable scientific interest in Tat's role in pathogenesis and to the present inventor's proposal that Tat may act as a powerful immunosuppressant in vivo.

A potential key to lentivirus Tat pathogenesis may involve in its ability to trigger apoptosis. Conventional Tat initiates apoptosis by stimulating the expression of Fas ligand (FasL, a monomeric polypeptide cell surface marker associated with apoptosis) on the T4 cell and macrophage surface. When FasL is cross linked by binding with Fas (the counter part to FasL which is also expressed on a wide variety of cell types), the apoptotic system is activated. Consequently, the death of these essential T4 cells and macrophages is accelerated, resulting in extreme immunosuppression. Thus, extracellular Tat's presence early in the course of HIV infection could reduce a patient's immune response, giving the virus an advantage over the host. Furthermore, the direct destruction of T4 cells and induction of $\alpha$-interferon production could help explain the lack of a robust cellular immune response seen in AIDS patients, as well as accounting for the initial profound immunosuppression.

Further support for this concept is found in a surprising new observation made by the present inventor who has demonstrated the Tat protein isolated from long term non-progressors is different from C-Tat found in AIDS patents. The Tat protein found in LTNP is capable of trans-activating viral RNA, however, LTNP Tat (designated herein after as IS-Tat for immunostimulatory Tat) does not induce apoptosis in T4 cells or macrophages and is not immunosuppressive. Moreover, T4 cells infected ex vivo with HIV isolated from LTNP (such cell lines are designated Tat TcL) can result in the over expression of IS-Tat proteins, often to the virtual exclusion of other viral proteins, that are strongly growth promoting rather than pro-apoptotic. The tat genes cloned from these Tat TcLs reveal sequence variations in two tat regions, at the amino terminus and within the first part of the second exon. These surprising discoveries could help explain why HIV infected LTNP T4 cells do not die off at the staggering rate seen in HIV infected individuals that progress to AIDS.

Additionally, variants of Tat are found in lentiviruses which infect monkey species yet do not result in the development immunodeficiency and epidemic infection. These variant Tat proteins direct monocyte differentiation into DCs which stimulate CTL responses. These simian Tat variants, and other Tat variants that are not immunosuppressive, have been termed attenuated or immunostimulatory Tat (IS-Tat).

Based on the observations with long-term CD4+ Tat T cell lines (Tat TcL), clinical observations, and experiments in animals, attenuated Tat (more specifically IS-Tat or, alternatively, Tat proteins that have been chemically or physically altered) may act as an immune stimulant activating T4 cells inducing their proliferation. This principle may help to explain the stable T4 levels seen in LTNP. Moreover, attenuated Tat may be useful as an adjuvant when co-administered with other active vaccine components such as, but not limited to, vaccines for other viruses, bacteria, rickettsia and cancer cells.

Cancers and chronic infections are the most prominent examples of common human diseases that respond to immune-based treatments. Although infections were the first diseases to be controlled by immunization, a series of clinical trials in humans starting in the 1980s have established that an immune response, particularly of the cytotoxic T lymphocyte (CTL) arm of the immune system, could regress some human melanomas (Phan C Q, et al., Cancer regression and autoimmunity induced by cytotoxic T lymphocyte-associated antigen 4 blockade in patients with metastatic melanoma, Proc Natl Acad Sc. USA 100:8372-7, 2003) and renal cancers. These observations were broadened by the discovery that dendritic cells (DC), a specific class of antigen-presenting cells (APC), are particularly effective at initiating CTL activity against cancers and other diseases (Banchereau J et al., Dendritic cells as vectors for therapy, Cell 106:271-4, 2001; Dalyot-Herman N et al., Reversal of CD8+ T cell ignorance and induction of anti-tumor immunity by peptide-pulsed APC, J Immunol 165:6731-7, 2000). Technologies that target and activate DC have yielded some early successes against human cervical pre-malignancies, caused by infection with Human Papilloma Virus (HPV) and human lung cancer. In contrast to chemotherapeutic drugs currently used against cancer, agents that provoke a CTL response against cancer potentially are accompanied by few side effects, owing to the great specificity of the immune response.

Efforts to develop immunotherapeutic drugs that treat cancer have been hampered by technical difficulties in targeting and activating DC to deliver and sustain the required entry signals to the CTL. Antigen targeting for the induction of a CTL response is a challenge insofar as natural processing requires that the antigen enter the cytoplasm of the cell in order to bind to the immune system's major histocompatibility complex (MHC) Class I antigen, a prerequisite to CTL activation because the ligand for activating the T cell receptor on CTL is a complex of antigen and MHC Class I. In almost all cases protein antigens, even when they are coupled with a DC co-activator, enter exclusively into the alternative MHC Class II antigen presentation pathway that excludes CTL stimulation. This can be overcome in part by peptide-based technologies, because peptides bind to MHC Class I that is already on the surface of the DC. However, this technology is non-specific and most peptides are poor DC activators which limits their efficacy as human treatments for cancer.

A limited group of biological proteins are known to stimulate a CTL response. Variants and derivatives of the Human Immunodeficiency Virus 1 (HIV-1) trans-activator of transcription (Tat) can stimulate this CTL response (Moy P et al., Tat-mediated protein delivery can facilitate MHC class I presentation of antigens, Mol Biotechnol 6:105-13, 1996; Fanales-Belasio E et al., Native HIV-1 Tat protein targets monocyte-derived dendritic cells and enhances their maturation, function, and antigen-specific T cell responses, J Immunol 168:197-206, 2002). Additional biologics that are currently known to directly trigger a CTL response are based on heat shock proteins (HSP) (Suzue K et al., Heat shock fusion proteins as vehicles for antigen delivery into the major histocompatibility complex class I presentation pathway, Immunol 94:13146-51, 1997; Stebbing J et al., Disease-associated dendritic cells respond to disease-specific antigens through the common heal shock protein receptor, Blood 102:1808-14, 2003), or on the outer coat protein of certain bacteria. Heat shock proteins have shown limited efficacy in the treatment of certain genital neoplasms related to HPV infection.

A large body of evidence implies that Tat is secreted from infected cells. Extracellular Tat is taken up by uninfected cells resulting in trans-activation of transcripts, a subset of which stimulate the cell (Frankel A D and Pabo C O, Cellular uptake of the Tat protein from Human Immunodeficiency Virus, Cell 55:1189-93, 1988) and a subset of which initiate programmed cell death. These observations demonstrate that Tat enters the cytoplasm of cells, where trans-activation is mediated, but they did not establish the key mechanism of entry via the receptor. The immediate immunosuppression that accompanies HIV infection has been attributed to Tat and has hindered the generation of successful HIV vaccines (Viscidi R P et al, Inhibition of antigen-induced lymphocyte proliferation by Tat protein from HIV-1, Science 146:1606-8, 1989; Cohen S S et al., Pronounced acute immunosuppression in vivo mediated by HIV-1 Tat challenge, Proc Natl Acad Sci USA 96:10842-47, 1999). Additionally, Tat suppression occurs at both the antibody level and at the T cell level and is antigen-specific. This distinguishes Tat-induced immunosuppression from other immunosuppressants currently used in human therapy, such as cyclosporine, that work exclusively on T cells.

Biological agents currently used to treat disease introduce foreign antigens (monoclonal antibodies, insulin, Factor VIII, organ transplants) into the body. An immune response against these antigens is undesirable because this immunity neutralizes, or in the case of organ transplants, rejects the foreign body in addition to causing collateral damage through allergic and autoimmune reactions. Recombinant proteins of human origin have been very successful in overcoming this problem and sustaining the efficacy of certain biological therapies such as insulin, Factor VIII, and monoclonal antibodies. However, even in these successes, undesired autoantibodies can still accumulate over time that limit or terminate efficacy. Methods to ameliorate these undesirable immune responses have not yet been developed.

Current immunosuppression treatment regimens are primarily designed for organ transplantation where a highly immunogenic foreign body often with multiple foreign antigens (histocompatibility antigens) must be maintained for the life of the patient. Up till the present time, this involves non-specific suppression of the entire immune system with multiple agents. Physicians and researchers have devised therapeutic regimens where a balance between the side effects of the immunosuppressants and organ rejection can be reached. The most common side effects associated with common immunosuppressive cocktails, which can include corticosteroids, cyclosporine and azathioprine, include stunted growth, weight gain, bone marrow inhibition, anemia, low white blood cell count and kidney damage. The most serious side effects, however, are infection, particularly with viruses and tumor formation due to the non-specific nature of the immune suppression. Therefore there exists a need to improved antigen-specific immunosuppressive therapies.

Autoimmune diseases are a series of unwanted immune responses that selectively destroy tissues. Severe autoimmune diseases are chronic, debilitating, and life-threatening. In some cases, specific agents that provoke a particular type of autoimmune disease are becoming defined. Approximately 2.5 million individuals currently suffer from rheumatoid arthritis (RA) in the US alone. Severe RA accelerates death rates at least five-fold compared to the general population (Wolfe F et al., Predicting mortality in patients with RA, Arth Rheumatism 48:1530-42, 2003). Peptide fragments from collagen type II, an important structural component in undamaged joints, can provoke RA in animals and could be developed as tolerizing agents for use against human RA (Van den Steen P et al., Cleavage of denatured natural collagen type II by neutrophil gelatinase B reveals enzyme specificity, post-translational modifications in the substrate, and the formation of remnant epitopes in rheumatoid arthritis, FASEB J 16:379-89, 2002).

Therefore, there exists a medical need for compositions which can be used as vaccines to specifically stimulate desired immune responses, such as in infectious diseases or cancer, and other compositions that suppress inappropriate immune responses to certain therapeutic, diagnostic or prophylactic agents and in autoimmune diseases in an antigen-specific manner.

SUMMARY OF THE INVENTION

For the purposes of clarification and to avoid any possible confusion, the HIV Tat as used in the compositions of the present invention will be designated as either "Tat" for conventional immunosuppressive Tat protein and "Tat*" or "ox-Tat*" for Tat that is genetically or chemically derivatized so that it is stimulatory. Additional abbreviations for Tat used in this disclosure include sTat (soluble Tat) and C-Tat (conventional native immunosuppressive Tat from HIV).

The present invention provides vaccines, adjuvants and immunotherapeutics for prophylaxis, diagnosis and treatment of infectious disease and cancer, tolerogen compositions for prevention and treatment of inappropriate immune responses to foreign and endogenous antigens and methods for the discovery of a new class of pharmaceutical agents, termed New Immunomodulatory Chemical Entities (NICE) which can duplicate the immunosuppressive activities of the Human Immunodeficiency Virus (HIV) trans-activator of transcription (Tat) and the immunostimulatory activities of Tat variants.

In an embodiment of the present invention, a method for identifying new immunomodulatory chemical entities (NICE) is provided comprising reacting a candidate NICE with a Tat SH3 binding domain wherein the Tat SH3 binding domain is bound to a solid phase to identify candidate NICE that bind to the Tat SH3, identifying the candidate NICE bound to the Tat SH3, adding the identified candidate NICE to a culture of purified peripheral blood monocytes, adding Tat having an SH3 binding domain to the peripheral blood monocytes and candidate NICE to form a test culture, incubating the test culture to allow the monocytes to differentiate into dendritic cells (DC) or regulatory macrophages (AReg), and removing the differentiated cells from the test culture and determining the presence or absence of DCs or AReg.

In another embodiment of the present invention, the Tat SH3 binding domain in the method for identifying NICE is selected from the group consisting of native immunosuppressive human immunodeficiency virus (HIV) Tat, simian lentivirus Tat, long-term non-responder Tat, randomly mutated HIV Tat and site-specific mutated HIV Tat.

In yet another embodiment of the present invention, the method for identifying NICE further comprised the step of injecting confirmed immunostimulatory NICE into an immunosuppressed mouse wherein the immunosuppression results from the presence of an endogenous SH3 binding domain. The immunosuppressed mouse can be a hairless (hr) mouse.

In an embodiment of the present invention, the method for identifying NICE further comprises the step of injecting a tolerogenic NICE into a mouse and further challenging the mouse with an antigen wherein tolerance results from the pre-treatment with tolerogenic NICE.

DETAILED DESCRIPTION OF THE INVENTION

Figure 1A:
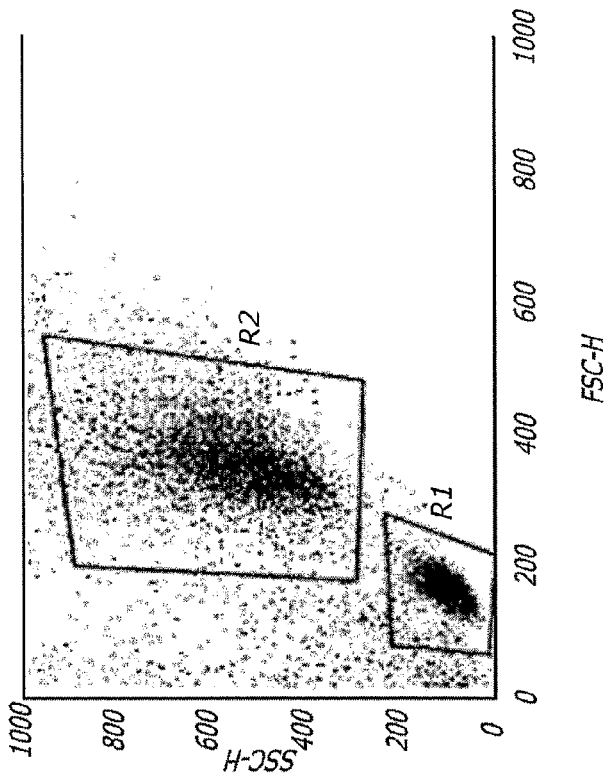
FIG. 1 depicts fluorescence activated cell sorter analysis of the results of Tat activation of monocytes according to the teachings of the present invention. Human peripheral blood monocytes were committed to differentiate into DCs through 5 days of culture in GM-CSF and IL-4. Committed DCs were cultured overnight either in medium alone (Control), LPS, or Tat, after which they were stained with an anti-CD86 antibody and analyzed by FACScan for CD86, a specific marker of DC activation, induction (left panel) or generalized activation (right panel, enlargement into box R2, shown for Tat-stimulated cells).

The present invention provides vaccines, adjuvants and immunotherapeutics for prophylaxis, diagnosis and treatment of infectious disease and cancer, tolerogen compositions for prevention and treatment of inappropriate immune responses to foreign and endogenous antigens and methods for the discovery of a new class of pharmaceutical agents, termed New Immunomodulatory Chemical Entities (NICE) which can duplicate the immunosuppressive activities of the Human Immunodeficiency Virus (HIV) trans-activator of transcription (Tat) and the immunostimulatory activities of Tat variants.

For the purposes of clarification and to avoid any possible confusion, the HIV Tat as used in the compositions of the present invention will be designated as either "Tat" for conventional immunosuppressive Tat protein and "Tat*" or "ox-Tat*" for Tat that is genetically or chemically derivatized so that it is stimulatory. Additional abbreviations for Tat used in this disclosure include sTat (soluble Tat) and C-Tat (conventional native immunosuppressive Tat from HIV).

The SH3 binding domain presents an important target for pharmaceutical development with the potential for the diagnosis, prophylaxis and treatment of undesirable cellular processes such as cancer and autoimmunity through small molecule intervention at discrete SH3 and SH2 domains (Koch, C. A. et al. (1991), "SH2 and SH3 domains: elements that control interactions of cytoplasmic signaling proteins," Science 252:668-74).

The present invention provides methods to derivatize, swap or mutate the SH3 binding domain of Tat for use as screening targets in the identification of small molecules that maintain or enhance DC function (immunostimulatory NICE) or that enhance AReg function (tolerogenic NICE). From this process, a library of closely-related molecules is created based on natural variants and random and induced mutations of Tat that can be used to differentially screen for NICE active at this motif. This library will allow the identification of NICE with high affinity for actively suppressive motifs (or dominant negative mutations competing for the same site) but not related, inactive, mutations with alternative binding specificities. The present invention provides a series of "filters" to identify high specific activity molecules and "filter out" molecules with poor specificity from the screening compound libraries. Both positive filters (suppressive motifs and related dominant negatives) and negative filters (inactive mutants and natural variants) are employed to isolate NICE with the most exact binding characteristics.

NICE scoring positive through the entire series of filters are validated by an in vitro functional biological assay (DC index), thereby insuring that drug candidates have the expected activities on cells (Example 6). The therapeutic activity of immunostimulatory NICE is then evaluated in vivo in the mouse strain hairless (hr). Mice expressing the hr gene mutation develop an acquired immune deficiency syndrome (AIDS)-like syndrome characterized by poor cytotoxic T lymphocyte (CTL) function, a shift in helper T lymphocytes from those regulating cell-mediated immunity (TH1) to those regulating antibody-mediated immunity (TH2) and increased susceptibility to chemical and ultraviolet light-induced skin cancers. After specificity and safety are established both in vitro and in vivo, immunostimulatory and immunosuppressive NICE can be tested clinically in human diseases including cancer, autoimmune diseases and infectious diseases.

The present inventor has unexpectedly demonstrated that HIV-1 Tat mediates two independent activities, a receptor-mediated triggering event at the cellular surface and an intracellular trans-activation activity that controls antigen-presenting cell (APC) differentiation. The receptor-mediated triggering event mediated by Tat is specific to APC, committing them for activation and differentiation into highly immunosuppressive antigen presenting cell regulatory macrophages (AReg) or into dendritic cells (DC) that stimulate specific cytotoxic T lymphocytes.

Antigen-presenting cells, macrophages and dendritic cells are critical in the pathogenesis or response to a variety of diseases, disorders and undesired immune responses. Tat triggers monocytes to differentiate into antigen-presenting macrophages expressing molecules that specifically suppress the immune response to the presented antigen(s). Treatment for human diseases may introduce foreign antigens (biologicals, including but not limited to, monoclonal antibodies, insulin, and erythropoietin) or tissues (including organ transplants and stents) where an immune response to the foreign agent is not desired. In autoimmune diseases, certain of the body's own endogenous molecules are incorrectly recognized as foreign, resulting in extensive inflammation and tissue damage. In one example, degradation of collagen type II into immunogenic peptides can trigger rheumatoid arthritis (RA) in animals and has been associated with human rheumatoid arthritis. Considerable research has centered on reducing the immune response to these proteins. It is the non-binding theory of the present inventor that the antigen-specific macrophage-induced suppression attributed to Tat can be applied to the reduction of the undesired immune response to certain foreign and endogenous molecules.

Unlike the current immunosuppressive therapies, the Tat-based compositions of the present invention have the potential to suppress antigen-specific immune responses without immunocompromising the patient. This is particularly important when chronic immunosuppressive therapy is needed, such as following organ transplantation or during autoimmune disease. This antigen-specific immune suppression requires a high specific activity tolerogen, which can be produced according to the teachings of the present invention. In the absence of a thorough understanding of the structure of the Tat molecule and the mechanism of Tat suppression, it has not been possible to rationally design and test tolerogens that maintain the specificity and activity of Tat. The present invention provides immunosuppressive, antigen-specific Tat-based compositions that have been designed and constructed using the recent findings on the Tat molecule by the present inventor. The Tat-based compositions of the present invention provide immune tolerance to a specific antigen exclusively while the remainder of the immune system remains intact and fully responsive.

The immunosuppressive effects of Tat are mediated by macrophages. When stimulated by Tat, either by natural HIV-1 infection or by Tat uptake, macrophages induce the Fas ligand (FasL), which in turn induce the programmed cell death (apoptosis) of antigen-reacting, Fas-expressing helper T cells (FIG. 3). Tat enhances the viability of cultured murine macrophages as long as the macrophages were first activated in vivo compared with no prior activation and stimulated with relatively high concentrations of Tat. By comparison, LPS promotes the viability of murine macrophages independently from in vivo stimulation, and at the same concentration effective for human macrophages. The Tat-based compositions of the present invention produces a stable suppression of mouse lymphocyte proliferation and may also serve to suppress an antigen-specific immune response to a variety of foreign antigens.

The macrophages responsible for these responses have been identified as antigen presenting cell regulatory macrophages (ARegs). ARegs are also known as "alternatively activated" macrophages (Tzachenis D et al., Blockade of B7/CD28 in mixed lymphocyte reaction cultures results in the generation of alternatively activated macrophages, which suppress T-cell responses, Blood 99:1465-73, 2002). ARegs are stable macrophages expressing FasL and secreting the cytokines IL-10 and IL-6 (Novak N et al., Engagement of FcεRI on human monocytes induces the production of IL-10 and prevents their differentiation in dendritic cells, J Immunol 167:797-804, 2001; Zhang H et al., Induction of specific T cell tolerance by Fas ligand-expressing antigen-presenting cells, J Immunol 162:1423-30, 1999). AReg are stable and respond in an autocrine and paracrine manner to these two cytokines, as well as in a paracrine manner to IL-4. These cytokines accumulate and switch the immune response from TH1 (based on helper T lymphocytes) to TH2 (based on suppressive T lymphocytes). As these cytokines build up they overwhelm and suppress the immune response and explain why immune responses are normally self-limiting in an antigen-specific manner.

An unexpected observation is that 1,000 fold lower concentrations of Tat (500 pM) trigger this effect on the macrophages, as compared with the concentration required to initiate direct apoptosis of CD4+ T cells (approximately 500 nM). Therefore, at concentrations of Tat achievable as a systemically administered immunomodulator, the macrophage effect will preferentially occur over the T cell effect.

The Tat-mediated antigen-specific suppression of the present invention is mediated through trans- (intracellular) activation of a CD14+FasL+macrophage. Example 3 of the present invention demonstrates that, in human cells, Tat-activated macrophages are immunosuppressive ARegs. At low concentrations of Tat (50 nM), Tat-induced immunosuppression was not only fully reversed by the addition of soluble Fas, but under these conditions, Tat actually became slightly stimulatory (relative to antigen treatment alone). Antibodies to FasL reversed Tat immunosuppression of tetanus responses and enhanced the *Candida* response relative to Tat treatment alone. Suppression could be fully reversed (>95% of control) with the further addition of anti-IL-10 and anti-IL-6 antibodies to the cultures, both cytokines deriving from macrophages under these culture conditions. The non-binding theory of the present inventor is that a portion of Tat-induced immunosuppression is contributed by induction of FasL, although other Tat-induced factors also could participate in suppressing T cell proliferative responses, especially at higher concentrations of Tat.

In order to make the Tat-based vaccines of the present invention, it is necessary to remove, modify, or override through mutation, the suppressive elements in Tat such that DC activation is maintained. Based upon structural resolutions, the present inventor describes a critical SH3 binding domain within the Tat sequence that controls the generation of a highly immunosuppressive antigen presenting cell regulatory macrophages (AReg). Simian lentiviruses related to HIV-1, but not causing immunodeficiency, have an alternative domain that is not suppressive. A mutant protein in a mouse strain (hairless, hr) that develops an immunodeficiency strikingly parallel to that seen in HIV-1 infection, including lost CTL and poor APC functions, encodes a SH3 binding domain homologous to HIV-1 Tat. This SH3 domain is proposed to control the differentiation potential of monocyte precursors either into DC that stimulate CTL, or AReg that suppress CTL. While prominent in HIV-1 infection, AReg are also now recognized as critical contributors to invasion of gastric (Ishigami S et al., Tumor-associated macrophage (TAM) infiltration in gastric cancer, Anticancer Res 23:4079-83, 2003), pancreas (von Bernstorff W et al., Systemic and local immunosuppression in pancreatic cancer patients, Clin Cancer Res 7:925s-32s, 2001), and ductal infiltrating breast tumors (Lin E Y et al., The macrophage growth factor CSF-1 in mammary gland development and tumor progression, J. Mammary Gland Biol Neoplasia 7:147-62, 2002; Visscher D W et al., Clinicopathologic analysis of macrophage infiltrates in breast carcinoma, Pathol Res Pract 191:1133-9, 1995), as well as components of tolerance in organ transplantation.

Recent surprising discoveries by the present inventor demonstrate that Tat can trigger CTL responses when Tat's DC stimulatory activity is isolated away from the suppression derived from AReg activation. It has not been previously possible to extend the in vitro activities of Tat to animals. One obstacle was a failure to understand that the cellular target of Tat activity was a precursor APC as opposed to the T cell, as had been widely believed. The present inventor determined that Tat stimulates APCs, as opposed to T cells and other cell types, at picomolar concentrations that are physiologic for in vivo activity. In vitro, APCs are approximately 1000 times more sensitive to Tat than T4 lymphocytes. Due to this discovery, one barrier to the successful use of Tat as an immunotherapeutic, namely achieving concentrations attainable in vivo, has been overcome. Thus, Tat has two activities that are the core of the present invention; APC targeting and induction of antigen-specific effects that result from APC activation.

Therefore, an embodiment of the present invention illustrated in Example 1 is that derivatized Tat* induces monocytes committed to the DC lineage to enlarge into activated, CD86+ DC APCs. The effect of derivatized Tat* on this population of cells is stimulatory, rather than suppressive, because the cells have been previously committed to become DCs. The present inventor has previously demonstrated that chemically derivatized Tat (Tat* or ox-Tat) is immunostimulatory in that it promotes differentiation of monocytes into dendritic cells, which subsequently leads to antigen-specific activation of cytotoxic T lymphocytes. Therefore properly derivatized Tat* resulting from chemical or genetic modifications, does not induce ARegs from monocyte APC precursors. Tat from HIV-1 long-term non-progressors (patients infected with HIV-1 who do not progress to Acquired Immune Deficiency Syndrome (AIDS)) and from certain related simian strains of lentivirus are also immunostimulatory rather than immunosuppressive. These natural variations in Tat are important source of sequence modifications for the genetically-derivatized Tat* of the present invention.

The present invention presents a model of Tat activation of dendritic cells leading to activation of tumor-specific cytotoxic T lymphocytes. Owing to its monocyte targeting specificity, Tat enters APC precursors, carrying along with it any other protein conjugated to it. At this step the APC is stimulated. Once inside the APC, Tat can leave the endosome, the reservoir for almost all soluble proteins, and enter the cytoplasmic space, as indicated through its transactivation of RNA expression. This trafficking property of Tat causes the initiation of major histocompatibility complex (MHC) class I presentation, since association with MHC class I also only occurs in the cytoplasm. The balance and duration of cellular gene activation determines whether the APC differentiates into an activated DC that potently presents for CTL activation, or into an AReg that shuts off CTL and other immune responses. In Example 1, the Tat*-Ag vaccine conjugate of the present invention is genetically derivatized to favor sustained DC activation and thereby to stimulate a superior CTL response against a cancer, in this case cervical cancer associated with Human Papilloma Virus infection.

Tat contains three distinct regions of interest (Kuppuswamy M et al., Multiple function domains of Tat, the trans-activator of HIV-1, defined by mutational analysis, Nucleic Acids Res 17:3551-61, 1989). The first region of interest is the transduction domain at the amino terminus of Tat (amino acids 3-19). A second region of interest is a cysteine-rich ligand binding domain (amino acids 22-37, SEQ ID NO. 7) which contains seven conserved cysteines. A third region of interest is the membrane translocation sequence (MTS) which encompasses amino acids 47-57. The complete amino acid sequence of HIV-1 Tat encoded by exons 1 and 2 of the Tat gene is depicted in SEQ ID NO. 1.

A proline rich stretch near the amino terminus (amino acids 3-19) of HIV-1 and HIV-2 Tat (SEQ ID NO. 3) within the transduction domain, has been described as a new SH3 binding domain having significant homology to the SH3-binding domain of the mouse hairless gene (hr) (SEQ ID NO. 4). Unexpectedly, mice expressing the hr gene mutation develop an AIDS-like syndrome characterized by poor CTL function, a shift in helper T lymphocytes from those regulating cell-mediated immunity (TH1) to those regulating antibody-mediated immunity (TH2) and increased susceptibility to chemical and ultraviolet light-induced skin cancers. Additionally, variants of Tat are found in lentiviruses that infect monkey species that do not develop immunodeficiency and that do not have epidemic infection. However, these variant Tat do not have the SH3 binding domain and instead substitute a different sequence, also set off by prolines at either end of the sequence, into the transduction domain. Therefore, this SH3 binding domain is central to the immunosuppressive activity of Tat. Genetic data indicates this SH3 binding domain regulates monocyte differentiation into AReg. In Tat proteins which do not contain this SH3 domain or this domain is mutated, monocyte differentiation is directed into DCs which stimulate CTL responses. It is this proline rich domain that is the focus of the NICE drug discovery process of the present invention.

It is also known that Tat contains a membrane translocation domain (MTS). After gaining access to the endosome following receptor binding, the MTS permits Tat to freely traffic across the endosomal membrane into the cytoplasm, where it transactivates gene expression, including but not restricted to genes of HIV-1 (Schwarze S R et al., In vivo protein transduction: delivery of a biologically active protein into the mouse, Science 285:1569-72, 1999). The MTS has been wrongly assumed to facilitate Tat entrance into the cell, which it can only accomplish at high concentrations that have been impossible to attain in vivo.

In an embodiment of the present invention, genetic derivatives of Tat, generated through modulating the signal transduction motif defined by the SH3 binding domain, are predicted to drive differentiation predominantly to dendritic cells or immunosuppressive AReg. AReg are also critical contributors to invasion of gastric, pancreas, and ductal infiltrating breast tumors, as well as components of tolerance in organ transplantation. It is a non-binding hypothesis of the present inventor that it is necessary to maintain the two external prolines at positions 3 and 18 flanking the SH3 domain in order to facilitate the proper structure for SH3 binding. In addition, the transduction domain from a non-immunosuppressive human variant Tat, or the domain from the hr mutation, can replace amino acids 3-19 of Tat, although the hr sequence (SEQ ID NO 4) is predicted to increase suppression. In addition, the stimulatory simian form of Tat (SEQ ID NO. 5), or its human equivalent sequence (SEQ ID NO. 6), can be substituted at this domain. Additional chemical modifications, such as ox-Tat, can be used for stimulation of dendritic/CTL responses and synthetic chemical moieties (NICE) can be constructed to generate an equivalent response.

The drug discovery process of the present invention has several distinct steps to differentially screen for NICE active at the SH3 domain. An SH3 mutational library will be constructed that allows the identification of high affinity NICE binding suppressive motifs (or dominant negative mutations competing at the same site) but not related, inactive mutations with alternative binding specificities. A first mutational library will be constructed on the basis of natural variance in the SH3 domain of HIV-1, some variants of which are less active at driving AReg formation, and some of which appear to compete against conventionally suppressive Tat (dominant negative mutations competing at the same site). A second series of mutations will be randomly generated, or generated by site-specific mutagenesis, to fill out the library. The sequences will be swapped through polymerase chain reaction (PCR) amplification methods well known in the art into a conventional suppressive Tat (HIV-1 MN), and characterized in the in vitro functional biological assay (DC index) developed by the present inventor and described in Example 6. The hybrid Tat demonstrating the highest DC index (most DCs and fewest ARegs) will be additionally evaluated for their activity in competing against native suppressive Tat co-administered to the same APCs. By this strategy, a series of related sequences will be defined having high affinity, reduced affinity, or no apparent affinity for the specific AReg SH3 domain.

Potential Tat-reactive NICE will be differentially screened by positive and negative selection against three progressive "filters." For the purposes of the present invention, as used herein, filters are defined as screening tiers through which NICE are positively or negatively screened for specific activity. The first filter for positive binding is conducted at relatively low stringency against the native SH3 binding domain (flanked within prolines). Native SH3 binding domains that induce ARegs are immobilized on a solid phase support and potential NICE, purchased in commercial libraries, are allowed to react in varying concentrations for a pre-determined time. Such binding assays are well known to those persons of skill in the art. Appropriate negative controls will be included so that specific binding can be determined and quantitated.

Libraries of potential Tat-reactive NICE suitable for use in the drug discovery process of the present invention include, but are not limited to, peptides and small organic synthetic molecules. These libraries can be purchased from vendors such as Sigma-Aldrich, St. Louis Mo., ActiMol, TimTec Corp., Newark Del., Tripos Inc., St. Louis Mo. and Mimotopes, San Diego Calif. and others that are known to persons skilled in the art.

This first positive filter screens a relatively broad number of candidate NICE. The second negative filter reduces and defines candidates by negative binding (flow through) a small series of inactive sequences that "filter out" non-specific NICE, which are trapped by the inactive domains immobilized on the solid support. In the third and final filter, NICE are positively reselected for binding non-identical active motifs, preferentially domains with high specific activity identified by their characteristics in the DC index assay. At this third filter stage, conditions are evaluated such as multimerization and buffering that could enhance high affinity interactions.

NICE scoring positive through the three filter screenings are then evaluated in the DC index biological assay for their ability to induce differentiation of monocytes into either immunostimulatory dendritic cells or immunosuppressive AReg macrophages. This assay is described in detail in Example 6. Appropriate positive and negative controls are included so that increases in the number of DCs or ARegs can be quantitated. In addition, the NICE are tested in a wide variety of doses from $0.01\text{-}10^6$ mM incubated with the monocytes from 1 hour to one week in order to determine those molecules that have optimal specificity, high specific activity, and favorable toxicity profiles.

Those NICE which are determined to preferentially direct monocyte differentiation into dendritic cells (immunostimulatory NICE) are evaluated for their ability to induce differentiation of dendritic cells in the hairless mouse model. This animal expresses endogenous SH3 domains and is immunocompromised. An immunostimulatory NICE of the present invention can overcome the SH3-induced deficiencies in dendritic cells. Mice will be injected with the NICE, or the NICE will be applied dermally, and subsequently challenged with a cutaneous irritant in delayed-type hypersensitivity assays well known in the art. These cutaneous lesions are first graded visually daily based on size and degree of redness. Skin biopsies are taken from 24 hours to one week after challenge and the number of DCs or Langerhan's cells determined histocytochemically with monoclonal antibodies specific for mouse DCs or Langerhan's cells. Appropriate positive and negative controls will be included and NICE injected in a wide dose range. The immunostimulatory NICE of the present invention can be administered to mice in this assay though means including, but not limited to intraperitoneal, subcutaneous, intradermal, oral, intranasal, cutaneous and intravenous routes. Those immunostimulatory NICE which perform to criteria in the hr mouse model will be considered candidates for immunotherapy of cancer or infectious diseases in humans.

In another embodiment of the present invention, immunostimulatory NICE are used as cancer adjuvants to be administered to patients to boost the immune response to tumor antigens when the construction of a cancer vaccine composition is not possible or inappropriate. The NICE adjuvant are administered admixed with the cancer antigen or administered in a different site than the cancer antigen. The cancer vaccine compositions and cancer adjuvant compositions of the present invention are administered to cancer patients in a variety of doses which will be determined after dose titration studies and methods of administration that will be optimized for the type of cancer.

Those NICE which are determined to preferentially, direct monocytes differentiation into ARegs (immunosuppressive NICE) are evaluated for their ability to induce tolerance after being administered along with the desired immunogenic antigen. The tolerogenic NICE compositions of the present invention will be evaluated for their ability to induce tolerance in normal mice. Mice are injected with tolerogenic NICE and immunogenic antigen via a route including, but not limited to, intraperitoneal, subcutaneous, intradermal, oral, intranasal, cutaneous and intravenous administration. From four hours to one week after receiving a tolerizing agent, the mice are challenged with the corresponding immunogenic antigen alone. This test assay will be performed with an antigen which is known to induce an immune response in normal mice, such as a human protein. After an appropriate amount of time, ranging from 72 hours to 2 weeks, the mice are sacrificed and both T and B lymphocyte responses to the immunogenic antigen are determined using assays well known to those skilled in the art. The immune response in these mice will be validated by challenging the mice with an unrelated antigen which is known to induce an immune response (such as *Candida*) and with antigen that is not expected to induce an immune response (such as a normal mouse protein). Only if the mice react appropriately to these controls will the tolerogenic NICE composition be considered effective. In variations of the above experiment, additional mice will be administered multiple doses of tolerogenic NICE composition before challenging with corresponding immunogenic antigen. It is anticipated that repeated administration of the tolerogenic NICE composition will be necessary to induce and maintain tolerance to certain antigens and this schedule of dosing is optimized for each antigen.

An additional therapeutic method to influence the SH3 control of dendritic cells involves activating RNA interference (RNAi), which results in sequence-specific degradation of the targeted double strand RNA (Fire A, RNA-triggered gene splicing, Trends Genet. 15:358-63, 1999; Zamore P D, RNA interference: listening to the sound of silence, Nat Struct Biol 8:746-50, 2001). Small interfering RNAs (siRNA) are RNA duplexes of 21-23 nucleotides which activate the RNAi pathway through their antisense strand and silence a gene through targeted degradation of its transcript. siRNAs are being widely developed as prophylactic and therapeutic agents to suppress selected RNA transcripts. Proposed targets include oncoproteins in cancer and infectious agents. The specificity and sensitivity of the target, an opening on the transcript free from secondary structure or complexed proteins that allows duplexed siRNA to form, and the actual delivery of the siRNA drug inside the cell are three critical factors governing the outcome of treatment. The sequence of the SH3 binding domain predisposing AReg/DC outcome is a potential RNAi target. Because the Tat's activity occurs at a balance point between stimulation (DC) and suppression (ARegs), small perturbations can be extremely efficacious.

An embodiment of the current invention is to create vaccine compositions for cancer and infectious disease therapy using the genetic sequences discovered from analysis of Tat to control DC vs. AReg outcome. Duplexed siRNAs are easily constructed from the sense strand of Tat and Tat variants using methods standard to those skilled in the art (Elbashir S M et al., RNA Interference is mediated by 21- and 22-nucleotide RNAs. Genes Devel 15:188-200, 2001). One of the obstacles associated with the successful therapeutic use of siRNAs is the difficulty targeting the siRNA to the target cell. The signal transduction domain and the MTS of Tat are proposed as targeting agents for siRNA. The DNA sequences disclosed in Example 7 and in SEQ ID NOs. 8, 9 and 10 are exemplary Tat targeting sequences.

The tolerogenic NICE compositions of the present invention can be produced with antigens implicated in a variety of autoimmune diseases. Autoimmune diseases which are within the scope of treatment with the tolerogenic NICE compositions of the present invention include, rheumatoid arthritis, diabetes, systemic lupus erythematosis, multiple sclerosis, inflammatory bowel diseases, psoriasis, scleroderma and autoimmune thyroid diseases Additionally the tolerogenic NICE compositions of the resent invention have the potential to treat other immune mediator diseases such as inflammation including, but not limited to, ocular inflammation and cardiac inflammation.

An antigen which elicits an immune response in a mammal can be incorporated into the tolerogenic NICE composition of the present invention. Suitable antigens include, but are not limited to, endogenous molecules such as those that illicit inappropriate immune responses in autoimmune diseases and foreign antigens. Non-limiting examples of foreign antigens that commonly elicit immune responses that limit their therapeutic potential include, but are not limited to, monoclonal antibodies (Mabs), carbohydrates, insulin, blood clotting factors, growth factors and hormones, enzymes and other diagnostic, therapeutic or prophylactic proteins. Carbohydrate antigens suitable for use in the tolerogen composition of the present invention include, but are not limited to, sialic acids.

Monoclonal antibodies suitable for use in the tolerogen compositions of the present invention include, but are not limited to, murine Mabs, human Mabs and humanized Mabs or Mabs produced from any mammal. Blood clotting factors suitable for use in the tolerogen compositions of the present invention include, but are not limited to, Factor VIII, Factor VII (rVIIa), Factor IX, Factor II, Factor VII, Factor IX, Factor X, von Willebrand Factor and Anti-inhibitor Coagulation Factor. Enzymes suitable for use in the tolerogen compositions of the present invention include, but are not limited to, asparaginase, collagenase, glutaminase, hyaluronidase, lysozyme, rhodanase, ribonuclease, β-lactamase, streptokinase, trypsin, uricase, urokinase, adenine deaminase, superoxide dismutase. Growth factors and hormones suitable for use in the tolerogen compositions of the present invention include, but are not limited to, human growth hormone, erythropoietin, granulocyte or macrophage stimulating factors, keratinocyte growth factor, interferons and interleukins.

One of skill in the art will recognize that the efficacy, or toxicity, of the compositions of the present invention, either alone or in combination with other pharmaceuticals, will influence the dose administered to a patient. Those of skill in the art may optimize dosage for maximum benefits with minimal toxicity in a patient without undue experimentation using any suitable method. Additionally, the compositions of the present invention can be administered in vivo according to any of the methods known to those skilled in the art including, but not limited to, injection, inhalation, infusion and orally or any of the methods described in exemplary texts, such as "Remington's Pharmaceutical Sciences ($8^{th}$ and $15^{th}$ Editions), the "Physicians' Desk Reference" and the "Merck Index."

The compositions can be formulated with any pharmaceutically acceptable excipients as determined to be appropriate by persons skilled in the art. Non-limiting examples of formulations considered with in the scope of the present invention include injectable solutions, lipid emulsions, depots and dry powders. Any suitable carrier can be used in the composition, which will depend, in part, on the particular means or route of administration, as well as other practical considerations. The pharmaceutically acceptable carriers described herein, for example, vehicles, excipients, adjuvants or diluents, are well known to those who are skilled in the art and are readily available to the public. Accordingly, there are a wide variety of suitable formulations of the composition of the present invention. The following formulations are exemplary and not intended to suggest that other formulations are not suitable.

Formulations that are injectable are among the preferred formulations. The requirements for effective pharmaceutical carriers for injectable compositions are well known to those of ordinary skill in the art (See Pharmaceutical and Pharmacy Practice, J.B. Lippincott Company, Philadelphia, Pa., Banker & Chalmers, Eds., pp. 238-50, 1982; ASHP Handbook on Injectable Drugs, Toissel, $4^{th}$ Ed., pp. 622-30, 1986). Such injectable compositions can be administered intravenously or locally, i.e., at or near the site of a disease, or other condition in need of treatment.

Topical formulations are well known to those of skill in the art and are suitable in the context of the present invention. Such formulations are typically applied to skin or other body surfaces.

The compositions of the present invention, alone or in combination with other suitable components can be made into aerosol formulations to be administered via inhalation. These aerosol formulations can be placed into pressurized acceptable propellants, such as dichlorodifluoromethane, propane, nitrogen and the like. The vaccine compositions of the present invention can also be formulated for dry powder inhalers. They also may be formulated for non-pressured preparations, such as in a nebulizer or an atomizer. Such spray formulations are particularly suitable for spray application to mucosa.

In addition to the above-described pharmaceutical compositions, the compositions of the present invention can be formulated as inclusion complexes, such as cyclodextrin inclusion complexes, or in liposomes (including modified liposomes such as pegylated and/or targeted liposomes).

It is within the scope of the present invention to provide compositions to a patient in need thereof through a plurality of routes of administrations using a plurality of formulations.

Additionally, the compositions of the present invention can be administered to patients in need of induction or suppression of specific immune responses according to dosing schedules known to persons skilled in the art, such as physicians. The scope of the present invention is considered to include administration of the compositions of the present invention either before, concurrent or after the onset of disease. The compositions of the present invention may be administered in a single dose or as repeated doses.

EXAMPLES

Example 1

Effects of Tat on the Dendritic Cell Lineage

Figure 1B:
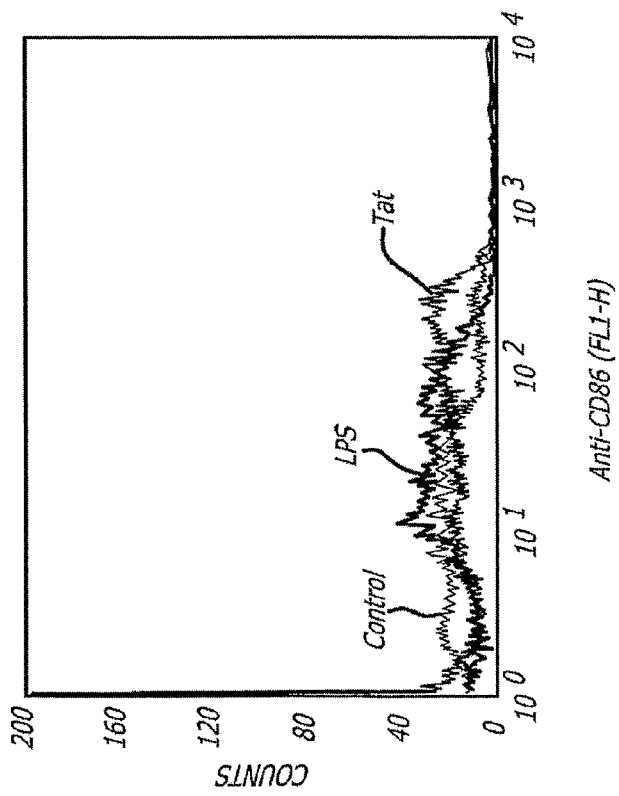

An additional embodiment of the present invention is that Tat induces monocytes committed to the dendritic cell (DC) lineage to enlarge into activated, CD86+ DC APCs (FIG. 1). Human monocytes enriched from PBMCs by Percoll density gradient separation and adherance to anti-CD14 coated magnetic beads (Dynabeads M-450, Dynal Biotech) were committed to differentiate into DCs through five days of culture in GM-CSF (100 ng/mL) and IL-4 (100 ng/mL). Committed DCs were cultured overnight either in medium alone (Control), LPS (100 ng/mL), or Tat (50 nM), after which they were stained with an anti-CD86 antibody (BD Pharmingen) and analyzed by FACScan for CD86 induction (left panel) or generalized activation (right panel, enlargement into box R2, shown for Tat-stimulated cells). The MFIs for CD86 expression are 9 (Control), 30 (LPS), and 187 (Tat), CD86 being a specific determinant of DC activation.

Figure 2:
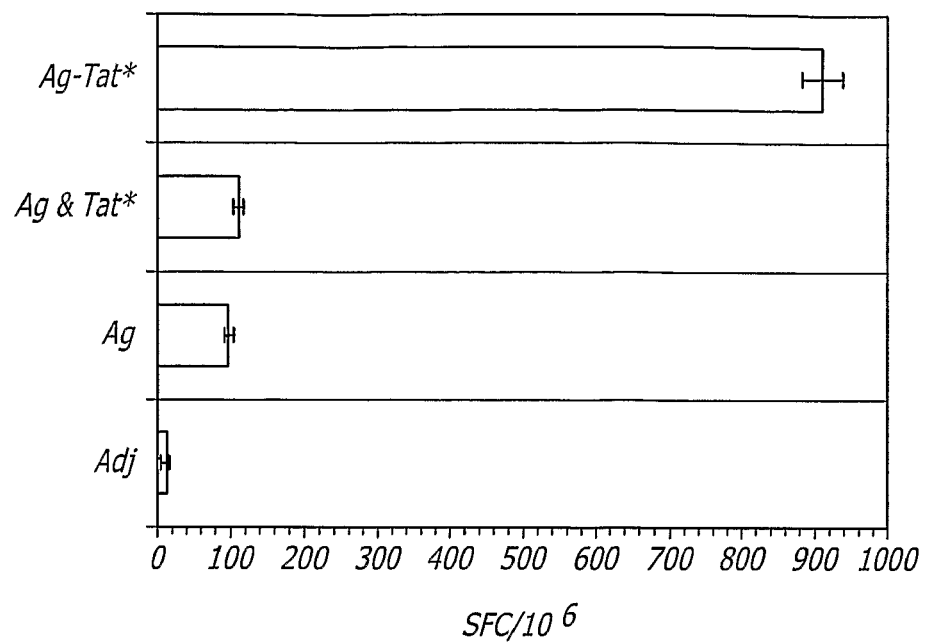
FIG. 2 depicts the enhancement of antigen-specific activation of CTLs by Tat*-antigen (Ag) complexes according to the teachings of the present invention. CTL activity was quantitated as the number of γ-interferon-secreting spot-forming colonies (SFC)/$10^6$ plated cells using ELISPOT assays.
Figure 3:
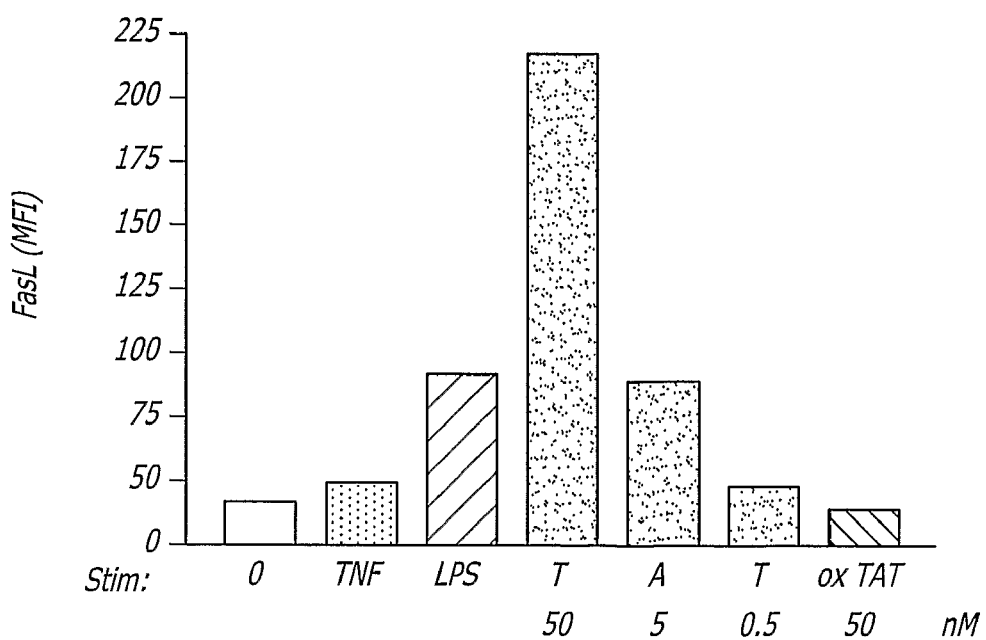
FIG. 3 depicts median fluorescence of monocytes, cultured for six days either with no stimulus (0), TNF-α, LPS, decreasing concentrations of C-Tat, or oxidized ox-C-Tat and stained with an anti-Fas ligand (FasL) monoclonal antibody (Mab) followed by a fluorescinated goat anti-mouse polyclonal antibody.

Derivatized Tat reduces AReg differentiation and potently enhances antigen-specific activation of CTLs (FIG. 2). Tat is chemically derivatized by oxidation (Tat* or ox-Tat) so that it does not induce ARegs from monocyte APC precursors (FIG. 3). Ten micrograms of Tat/p24 Tat*-Ag conjugate (Ag-Tat*) was administered into the flanks of Balb/C mice in adjuvant on day 0 and day 7. Experimental groups were comparatively immunized in adjuvant with 5 μg of p24 in one flank and 5 μg derivatized Tat in the other flank (Ag & Tat*), or 10 μg of p24 in adjuvant (Ag). Control mice were given two injections of adjuvant. Four mice were treated in each group. At day 14, draining lymph node cells from each animal were harvested and re-stimulated overnight in cultures of irradiated Ap24 (H-2d cells stably transfected to express antigen p24) cells or control non-transfected cells. CTL activity was quantitated as the number of γ-interferon secreting spot forming colonies (SFC)/$10^6$ plated cells using ELISPOT assays. The background with non-transfected re-stimulators, which was in all cases <10 SFC/$10^6$, is subtracted from each point. The results are indicative of three similar experiments.

Example 2

Tat Activation of Macrophages and Suppression of the Immune Response

Recombinant Tat protein is prepared as previously described (Li, C. J. et al. (1995), "Induction of apoptosis in uninfected lymphocytes by HIV-1 Tat protein," Science 268: 429-31) under mildly denaturing conditions and was renatured in the presence of 0.1 mM DTT.

Tat activation of monocytes is dose-dependent and saturatable (FIG. 3). Human monocytes were cultured in increasing concentrations of recombinant Tat for six days at which time they were assayed for Fas ligand (FasL) induction as a measure of activation by using flow cytometry (FACScan, Becton Dickinson) to quantitate the intensity of staining (mean fluorescence index (MFI)) with an anti-Fas ligand monoclonal antibody (Nok 1, BD Pharmingen). Higher concentrations of Tat did not increase MFI (not shown), and T cells could not be activated with 50 nM Tat (not shown), the plateau stimulatory concentration for APCs.

Figure 4A:
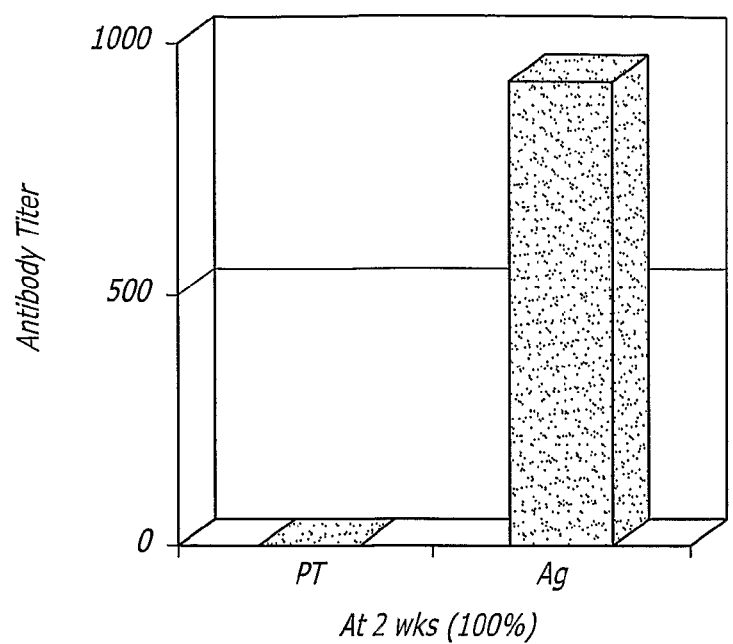
FIG. 4A-B depict antibody titer to an immunogenic antigen in the presence of the tolerogen composition of the present invention (PT) or with non-immunosuppressive ox-Tat* (Ag).
Figure 4B:
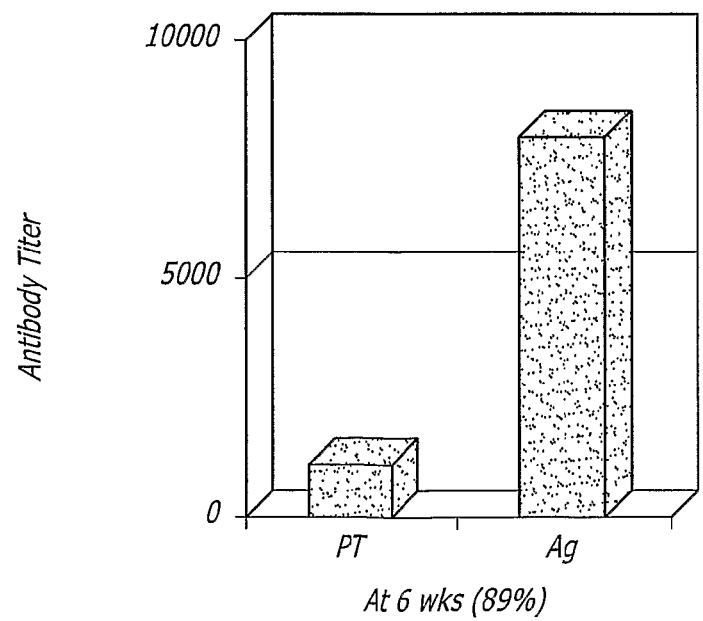

Tat suppresses the antigen-specific humoral immune response to HIV-1 p24 (FIG. 4). At week 0, mice (4 in each group) were immunized with 5 µg recombinant p24 protein (Chiron, Emeryville, Calif.) and either 5 µg recombinant Tat protein (PT) or 5 µg recombinant ox-Tat* protein (Ag) mixed in 100 µL complete Freund's adjuvant and administered subcutaneously in the flank. Following immunization, sera were collected every other week for 10 weeks and assayed for a specific antibody response to p24 by commercially available ELISA (Abbott Laboratories, Abbott Park, Ill.). The p24 antibody titer at 2 weeks (FIG. 4A) was completely suppressed by the Tat protein (PT) compared with the ox-Tat* control (Ag). This response was maintained for at least 6 weeks. The antibody titers at 6 weeks are approximately ten times greater than at week 2 due to maturation of the immune response.

Figure 5:
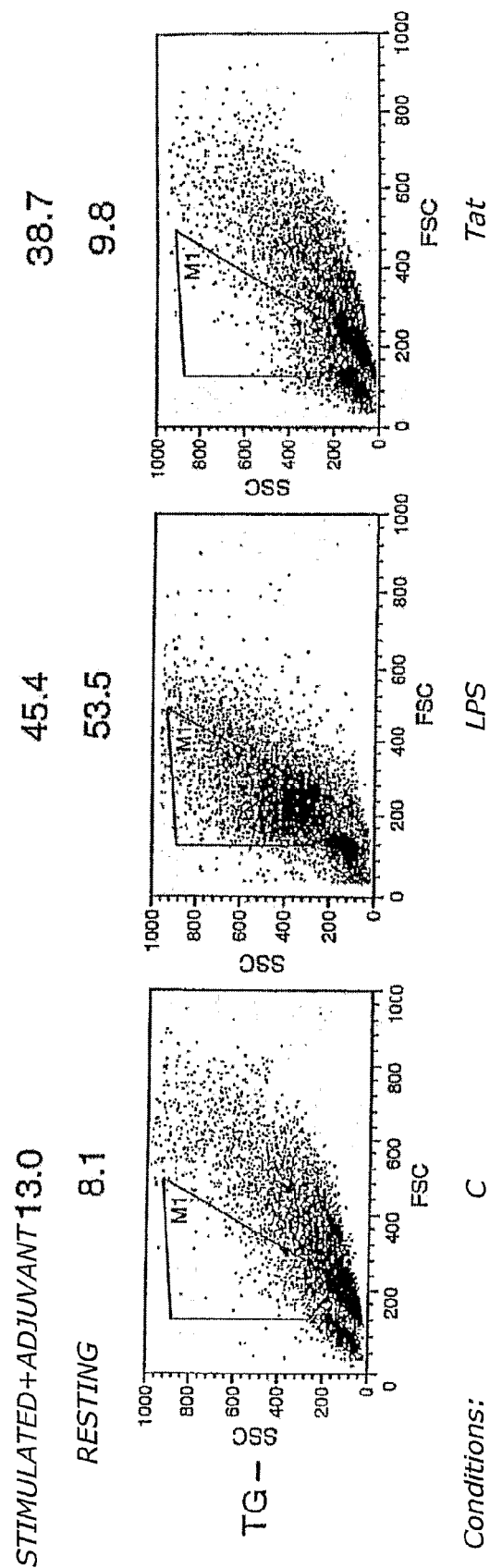
FIG. 5 depicts fluorescence-activated cell sorter analysis of mouse peritoneal macrophages that were isolated either after in vivo thioglycolate stimulation (Stimulated+adjuvant) or without in vivo stimulation (resting). Mouse peritoneal macrophages were cultured for five days either in the absence of additional stimulation (C), with LPS or with Tat. Activation was determined as percent enlarged cells (M1 fraction).

Tat enhances the viability of cultured murine macrophages as long as the macrophages were first activated in vivo compared with no prior activation and stimulated with relatively high concentrations of Tat (FIG. 5). APCs were isolated by peritoneal lavage from mice intraperitoneally injected four days earlier with either 2.9% thioglycolate (as adjuvant) or 0.85% saline solution (resting). Harvested washout cells were cultured at $10^6$ cells/mL for five days in medium alone (Control, C), lipopolysaccharide (LPS, 100 ng/mL), or Tat produced as recombinant protein in *E. coli* (Tat, 500 ng/mL). Activation was determined as % enlarged cells (M1 fraction).

Figure 6:
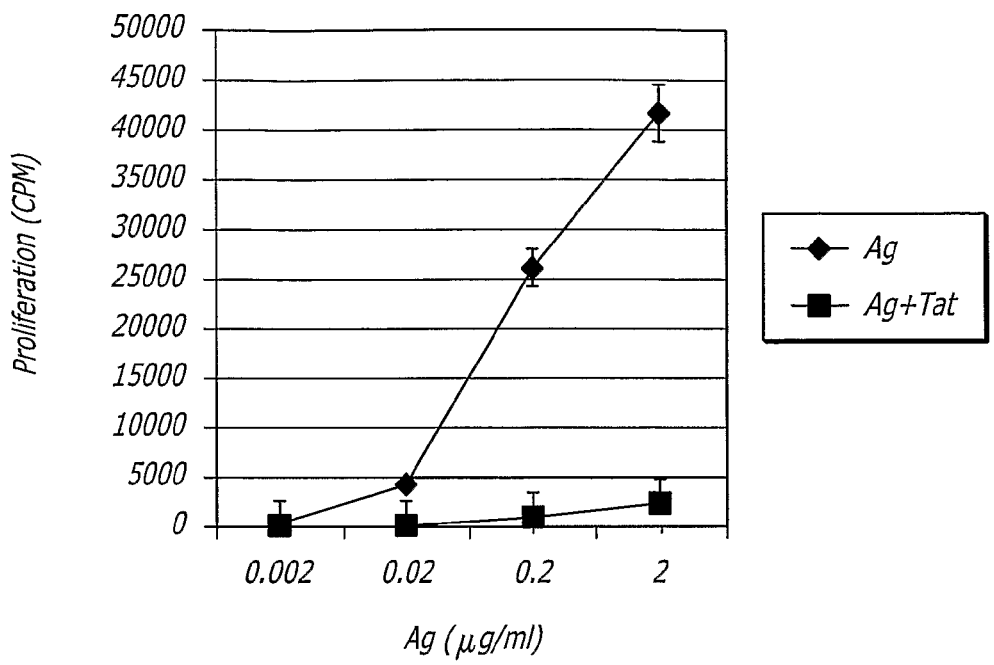
FIG. 6 depicts stable suppression of antigen-stimulated T lymphocytes by Tat-Ag complexes two weeks after immunization with the tolerogen compositions of the present invention.

The Tat tolerogen of the present invention produces a stable suppression of mouse lymphocyte proliferation (FIG. 6). Mice were immunized in quadruplicate with a Freund's adjuvant emulsion containing either 5 µg Tat/p24 (recombinant HIV-1 gag protein p24) tolerogen (GRP 2) or with 5 µg avidin-p24 (GRP 1) as control. At two weeks residual draining lymph node cells were harvested, pooled within each group, and cultured at $10^5$ cells/microtiter well for four days in the presence of graded concentrations of recombinant p24 protein (p24, µg/mL). Proliferation was assayed as a determinant of recall T cell response by quantitating overnight $^3$H thymidine uptake (CPM) in a liquid scintillation counter. This response is maintained for up to six weeks.

Figure 7:
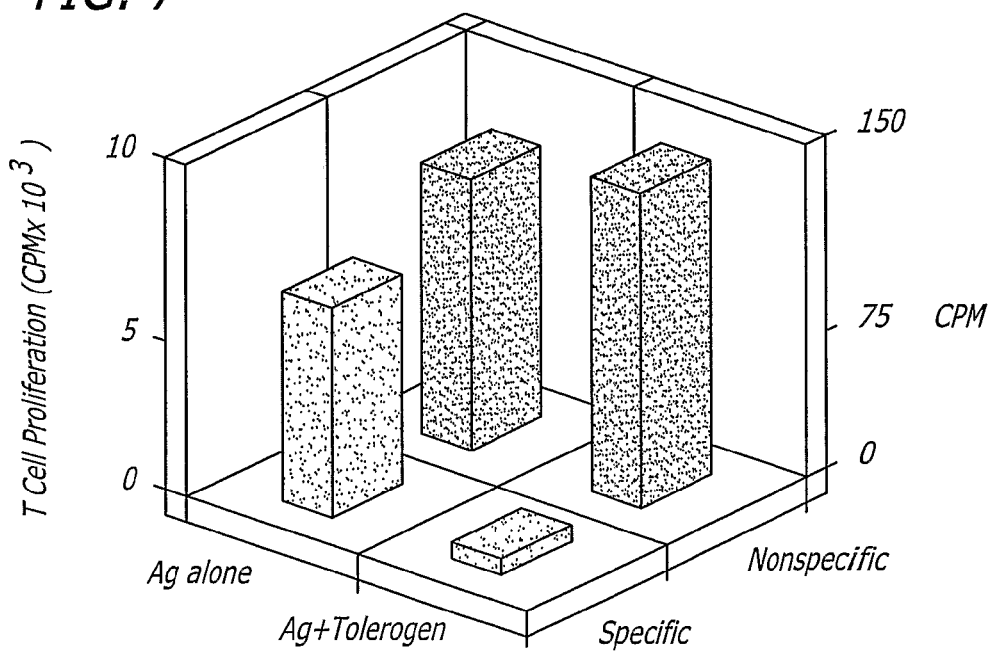
FIG. 7 depicts the antigen-specificity of Tat suppression according to the teachings of the present invention. Mice were immunized at day 0 and boosted at day 7 with an adjuvant emulsion containing either Tat (Ag+Tat), or with Ag Alone as control. At day 14, draining lymph node cells were harvested and stimulated with either specific or non-specific antigen and proliferation measured by $^3$H thymidine uptake (CPM) after four days of culture.

In addition, the Tat tolerogen of the present invention generates an antigen-specific immune suppression (FIG. 7). Mice in quadruplicate were immunized at day 0 and boosted at day 7 with an adjuvant emulsion containing either 5 µg Tat/p24 tolerogen (Ag+Tol) or with 5 µg avidin-p24 (Ag Alone) as control. At day 14, draining lymph node cells were harvested and stimulated at $10^5$ cells/microtiter culture well either with added antigen (Specific, recombinant p24, 1 µg/mL) or with added anti-T cell receptor monoclonal antibody (NonSpecific, 2C11, 10 µg/mL). Tritiated thymidine uptake (CPM) was determined by liquid scintillation at day 4 of culture. The specific Ag+Tol response is suppressed 98% relative to Ag alone, and is not distinguishable from cells cultured in the absence of stimulants.

Example 3

Tat Suppression is Mediated by ARegs

Figure 8:
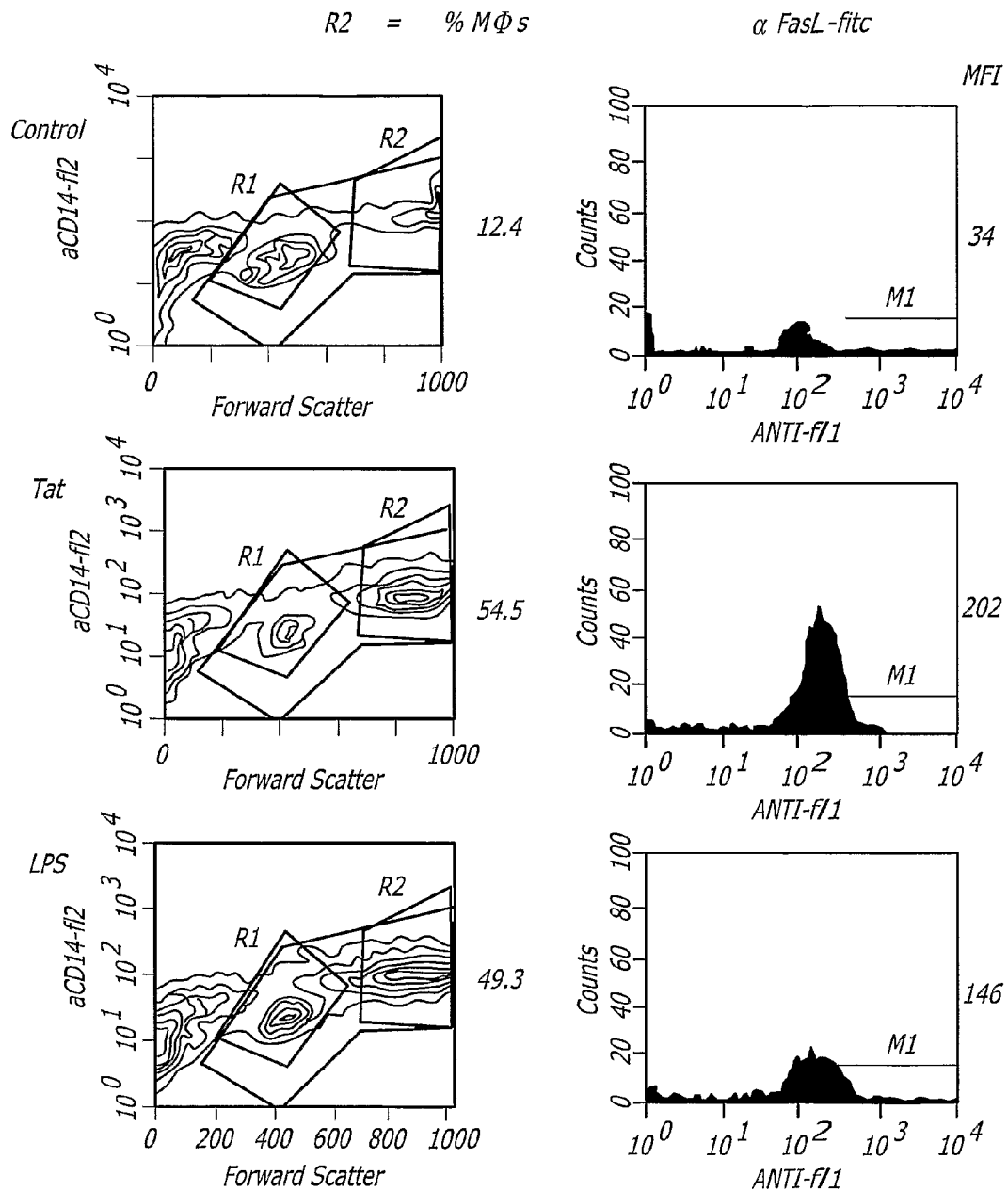
FIG. 8 depicts fluorescence-activated cell sorter analysis of human peripheral blood monocytes cultured for four days in control medium (Control), or medium containing Tat or LPS according to the teachings of the present invention. Harvested cells were doubly stained with a fluoresceinated anti-FasL Mab (αFasL-fitc) and with an anti-CD14 rhodamine labeled Mab. Cells were analyzed by FACScan for activation (forward scatter), CD14 expression (% macrophages, R2), and for induction of FasL (MFI). The T cell population is labeled R1.

The Tat mediated antigen-specific suppression of the present invention is mediated through trans- (intracellular) activation of a CD14+FasL+macrophage (FIG. 8). In mice, Tat tolerizes at the T cell level and is maintained for at least six weeks after the initial treatment under the conditions demonstrated in FIG. 6. A human peripheral blood mononuclear cell (PBMC) population enriched for monocytes by Percoll centrifugation was cultured for four days either in medium containing 5% fetal calf serum (FCS, Control), Tat (50 nM), or LPS (100 ng/mL). Harvested cells were doubly stained with a fluoresceinated (anti-fl1) anti-FasL monoclonal antibody (Mab), (αFasL-fitc, Nok 1, BD Pharmingen) and with an anti-CD14 rhodamine labeled Mab (αCD14fl2, BD Biosciences, CD14 being a determinant specific to macrophages (Mφ). Cells were analyzed by FACScan (Becton Dickinson) for activation (Forward Scatter), CD14 expression (R2, percent Mφs), and for induction of FasL (MFI). The T cell population (R1) was CD14- and did not express FasL. Similar results were obtained from cells harvested after 2, 3, 5, or 6 days of culture as for PBMCs harvested at day four.

Figure 9A:
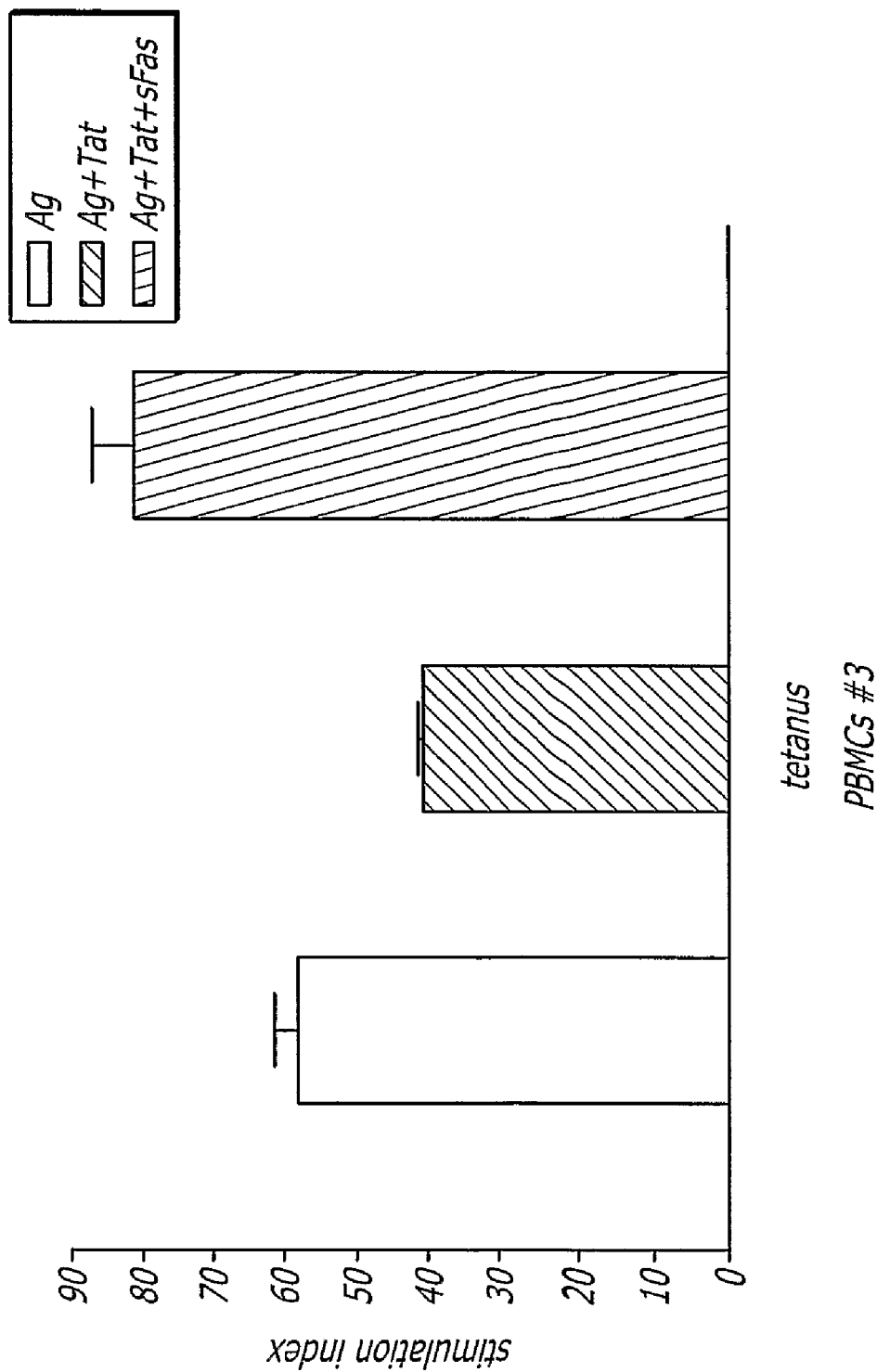
FIG. 9A-B depicts the regulatory and immunosuppressive characteristics of Tat-activated macrophages according to the teachings of the present invention. (A) Human polymorphonuclear neutrophils (PBMC) from one individual (PBMCs #3) cultured for 5 days in either medium with tetanus antigen (Ag), antigen with the further addition of Tat (Ag+Tat) or Ag with Tat and recombinant sFas protein (Ag+Tat+sFas). The results are graphed as stimulation index (mean cpm stimulated culture/mean cpm medium control). (B) Proliferation of PBMCs cultured 6 days with either tetanus or *Candida* antigen alone (Ag), compared with cultures in which Tat (Ag+Tat), or Tat and the antagonistic anti-Fas antibody, ZB4, were added (Ag+Tat+αFas).
Figure 9B:
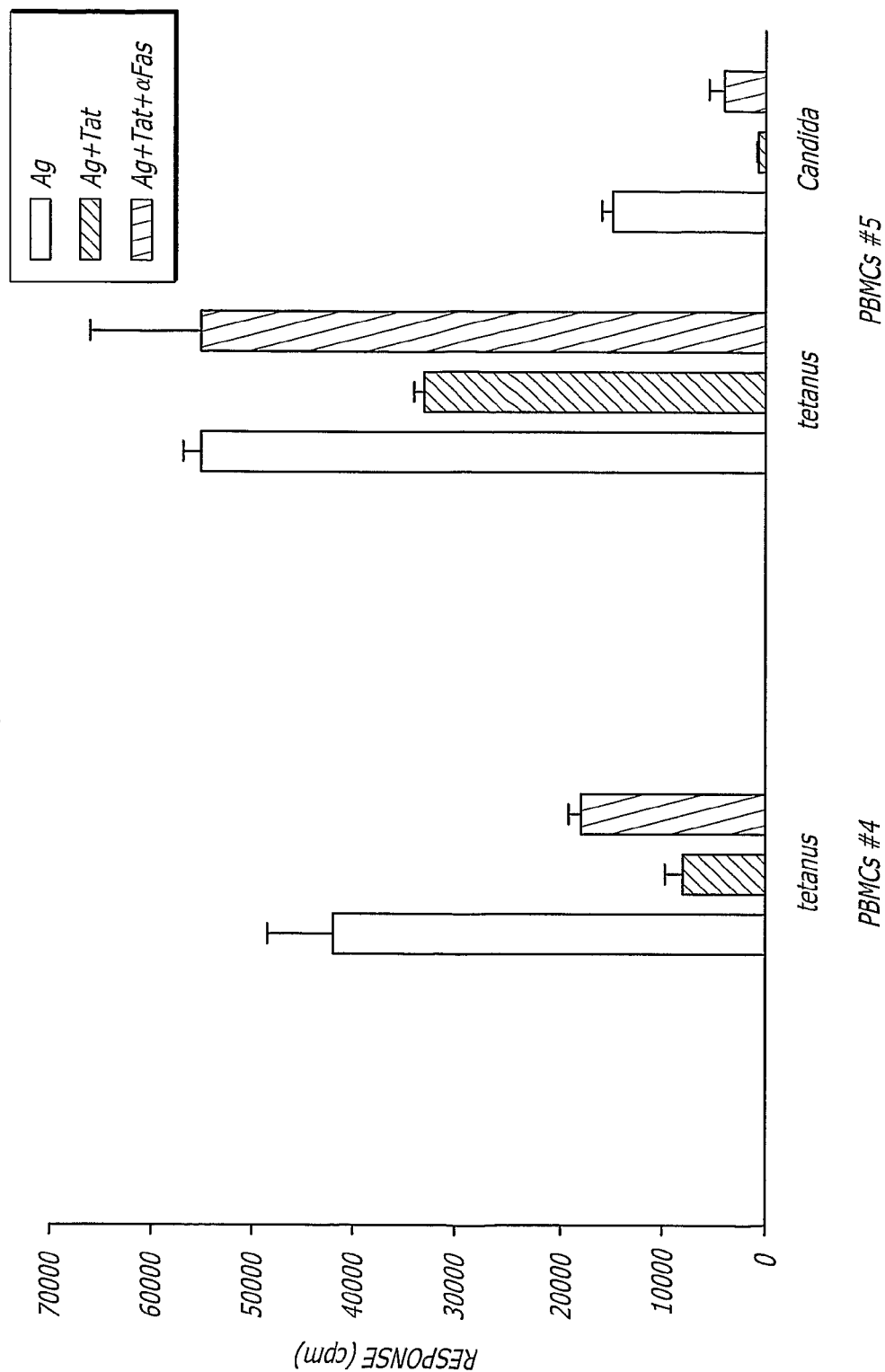

The present invention demonstrates that, in human cells, Tat-activated macrophages are regulatory and immunosuppressive APC macrophage regulators (ARegs) (FIG. 9). To define the pathway of Tat immunosuppression, through FasL induction on the macrophage, resulting in loss of helper T cell recall responses, T cell proliferation assays are used with recall antigens, tat and FasL antagonists. FIG. 9A: Human PBMCs from one individual were cultured in triplicate for 5 days in either medium (not shown), tetanus antigen (Ag, 0.3 Lf/mL), antigen with the further addition of 50 nM Tat (Ag+Tat) or Ag with 50 nM Tat and recombinant sFas protein (25 µg/mL) to block surface Fas L expressed on macrophages (Ag+Tat+sFas). Tritiated thymidine was added over the last 18 hours, and results are graphed as stimulation index (mean cpm stimulated culture/mean cpm medium control). Results are representative of three similar experiments. At low concentrations of Tat (50 nM), Tat-induced immunosuppression was not only fully reversed by the addition of soluble Fas, but under these conditions, Tat actually became stimulatory (141% relative to antigen treatment alone). FIG. 9B: Proliferation of PBMCs cultured 6 days with either tetanus or *Candida* antigen alone (Ag), compared with cultures in which Tat (Ag+Tat, 125 nM), or Tat (125 nM) and the antagonistic anti-Fas antibody, ZB4 (250 µg/mL, Upstate Biotechnology) also were added (Ag+Tat+αFas). Results are representative of three similar experiments.

Example 4

Sequence and Homology Features of the Tat Protein

The complete amino acid sequence of HIV-1 Tat encoded by exons 1 and 2 of the Tat gene is listed below:

```
ATG GAG CCC GTG GAC CCT CGC CTG GAG CCC TGG AAG CAC CCG GGC AGC      SEQ ID NO. 1
Met Glu Pro Val Asp Pro Arg Leu Glu Pro Trp Lys His Pro Gly Ser      SEQ ID NO. 2
1           5                   10                  15
```

```
CAG CCC AAG ACC GCC TGC ACC ACA TGT TACT GC AAG AAG TGC TGC TTC
Gln Pro Lys Thr Ala Cys Thr Thr Cys Tyr Cys Lys Lys Cys Cys Phe
            20/60            25                30/90

CAC TGC CAG GTG TGC TTC ACC AAG AAG GCC TTG GGC ATC AGC TAC GGC
His Cys Gln Val Cys Phe Thr Lys Lys Ala Leu Gly Ile Ser Tyr Gly
        35              40/120                45

CGC AAG AAG CGC CGG CAG CGC CGC CGG GCC CCT GAG GAC AGC CAG ACC
Arg Lys Lys Arg Arg Gln Arg Arg Arg Ala Pro Glu Asp Ser Gln Thr
    50/150              55                  60/180

CAC CAG GTG AGC CCT CCC AAG CAG CCC GCT CCA CAG TTC CGC GGC GAC
His Gln Val Ser Pro Pro Lys Gln Pro Ala Pro Gln Phe Arg Gly Asp
65                  70/210            75                  80/240

CCT ACC GGT CCC AAG GAG AGC AAG AAG AAG GTG GAG CGC GAG ACC GAG
Pro Thr Gly Pro Lys Glu Ser Lys Lys Lys Val Glu Arg Glu Thr Glu
                85                  90/270            95

ACC CAT CCC GTC GAC
Thr His Pro Val Asp
            100/300
```

The Tat of the present invention has a proline (P) rich segment near the amino terminus (amino acids 3-19):

```
                                              (SEQ ID NO. 3)
Pro Val Asp Pro Arg Leu Glu Pro Trp Lys His Pro

Gly Ser Gln Pro Lys
```

Figure 12:
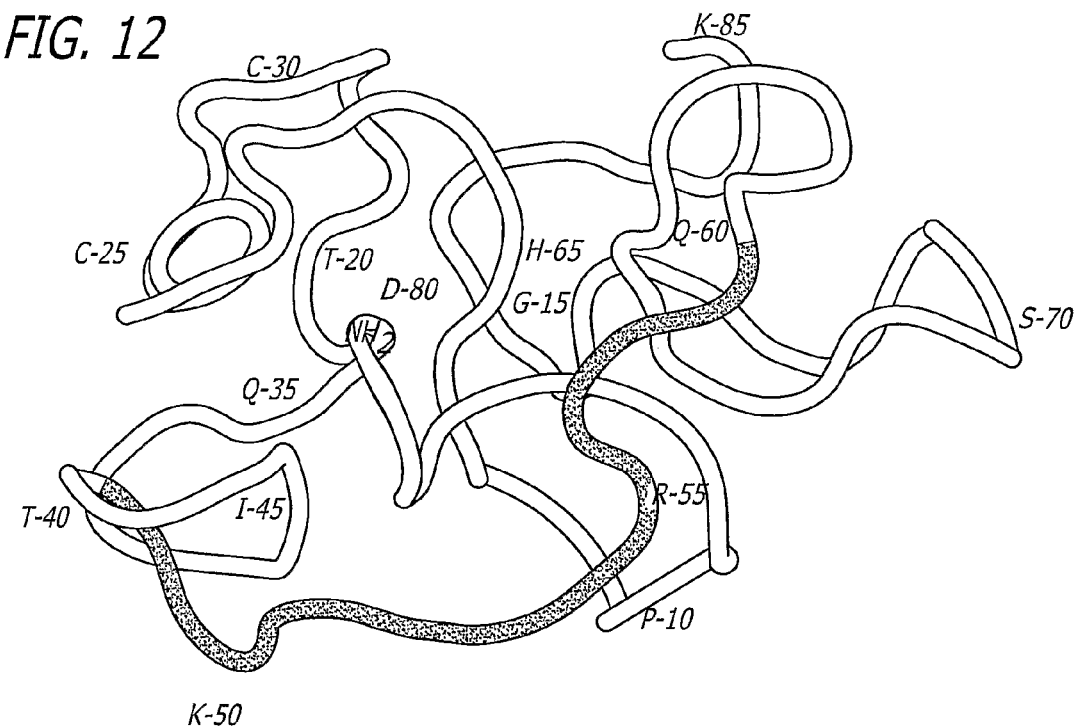
FIG. 12 depicts domain 3 of the Tat molecule, the membrane translocation sequence, amino acids 47-57 as indicated by the hatched portion of the molecule.
Figure 15:
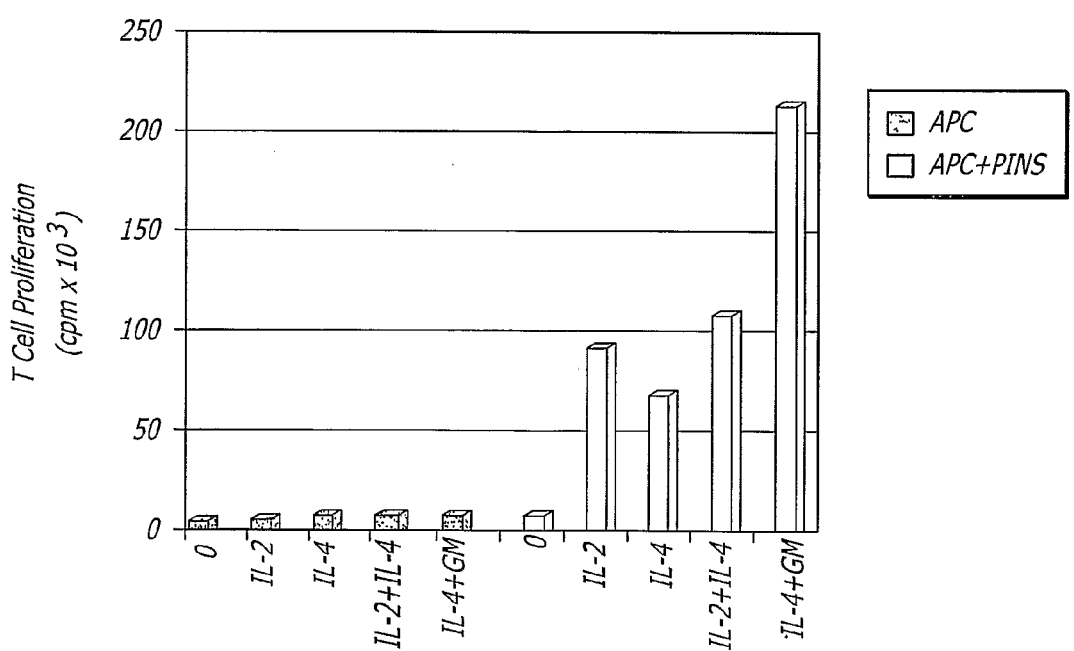
FIG. 15 depicts re-activation of T lymphocytes by cytokines and vaccine compositions made according to the teachings of the present invention.
Figure 13A:
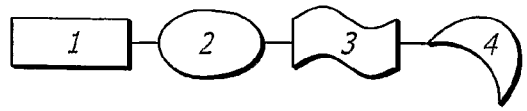
FIG. 13 schematically depicts the construction of vaccine and tolerogen cassettes according to the teachings of the present invention. Panel A: Domains of native Tat. Panel B: Varying antigen cassettes for the production of the vaccines or tolerogens of the present invention. The immunostimulatory or immunosuppressive functions of domain 1 (SH3 binding motif) will determine if the resultant protein is a vaccine (immunostimulant) or tolerogen (immunosuppressive).
Figure 13B:
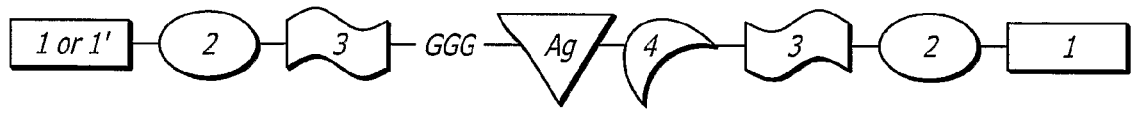
Figure 13B:
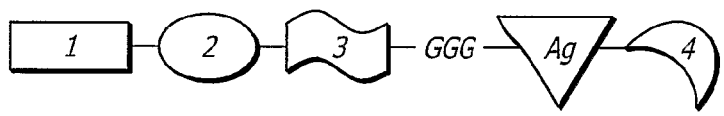
Figure 13B:
Figure 13B:
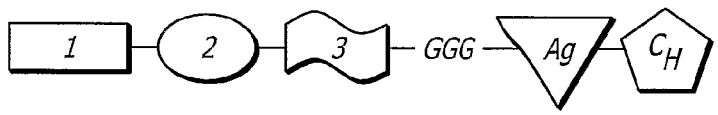
Figure 13B:
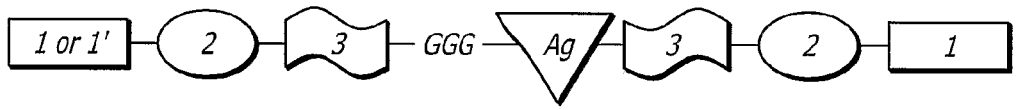
Figure 13B:
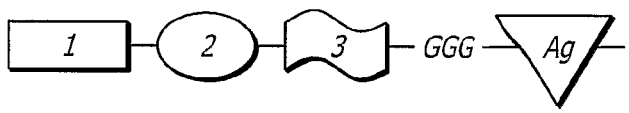
Figure 13B:
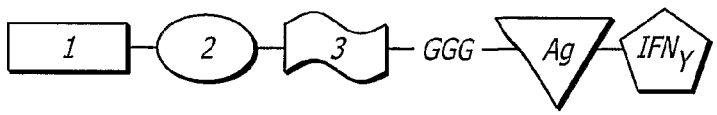
Figure 14:
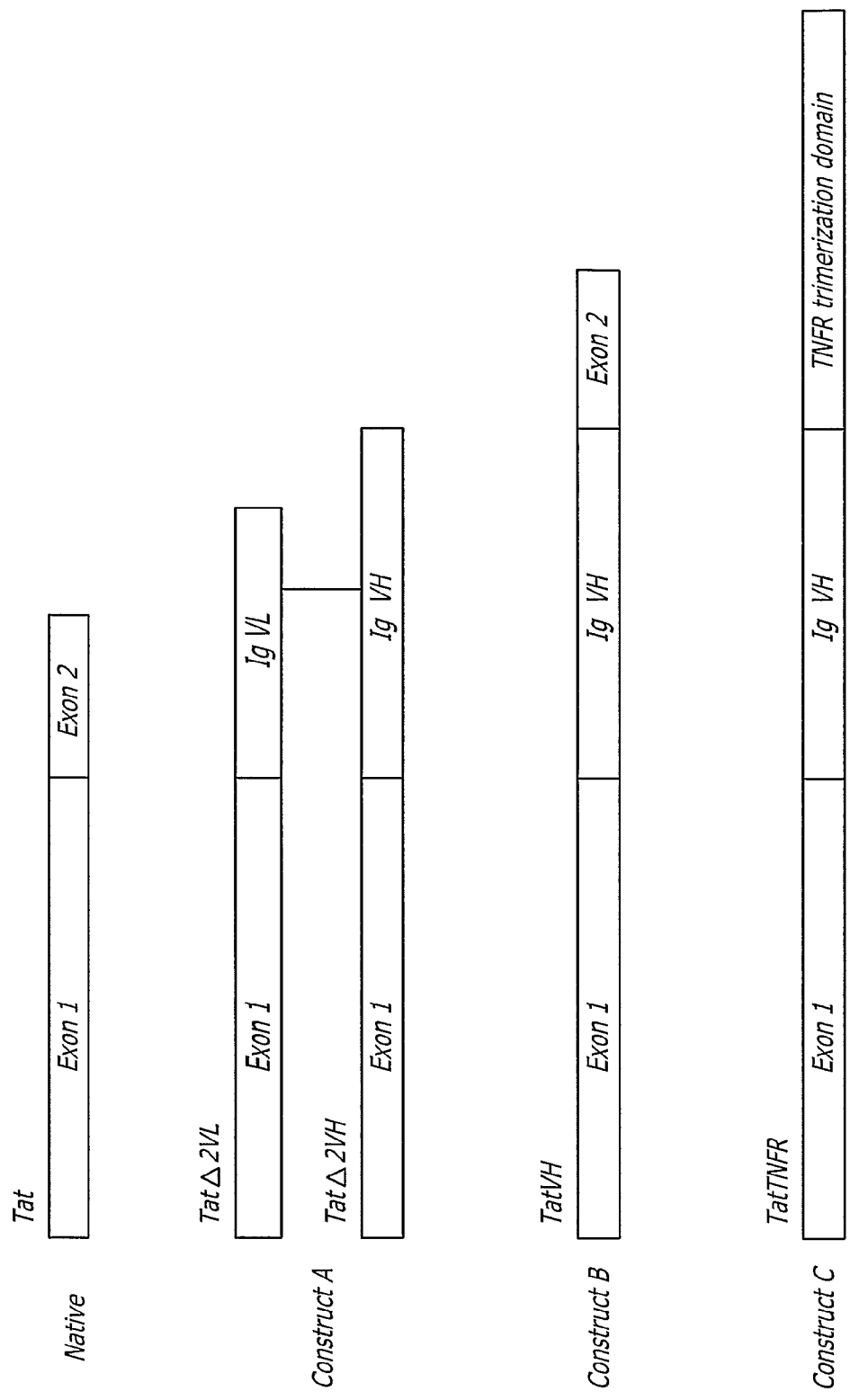
FIG. 14 depicts tolerogen composition constructs according to the present invention specific for preventing immune responses to human or humanized monoclonal antibodies.
Figure 16A:
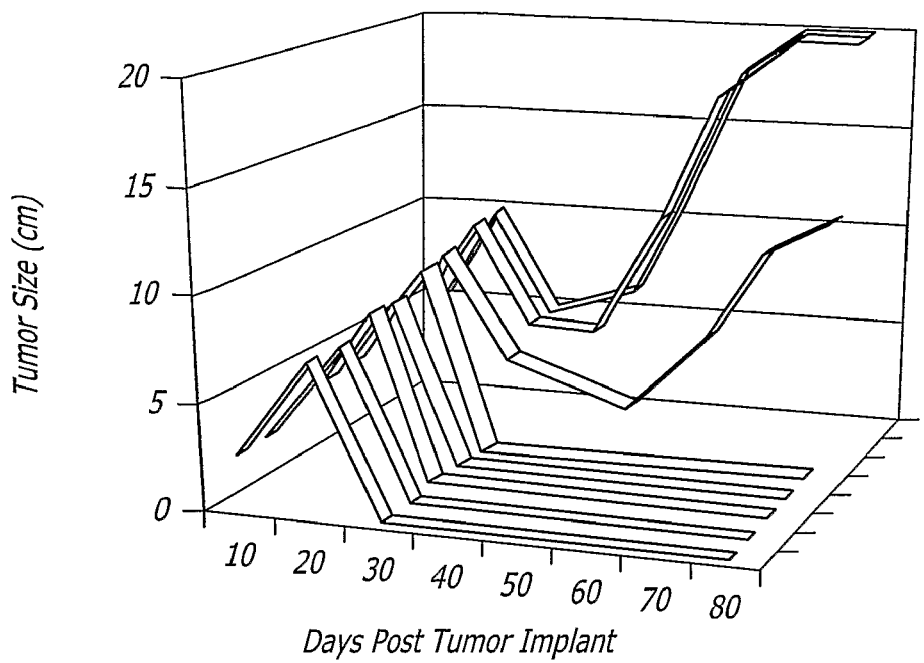
FIG. 16 depicts the efficacy of cancer vaccine compositions made according to the teachings of the present invention in shrinking tumor size and improving survival in a mouse model of cervical cancer (FIG. 16A).
FIG. 16B depicts control treated mice.
Figure 16B:
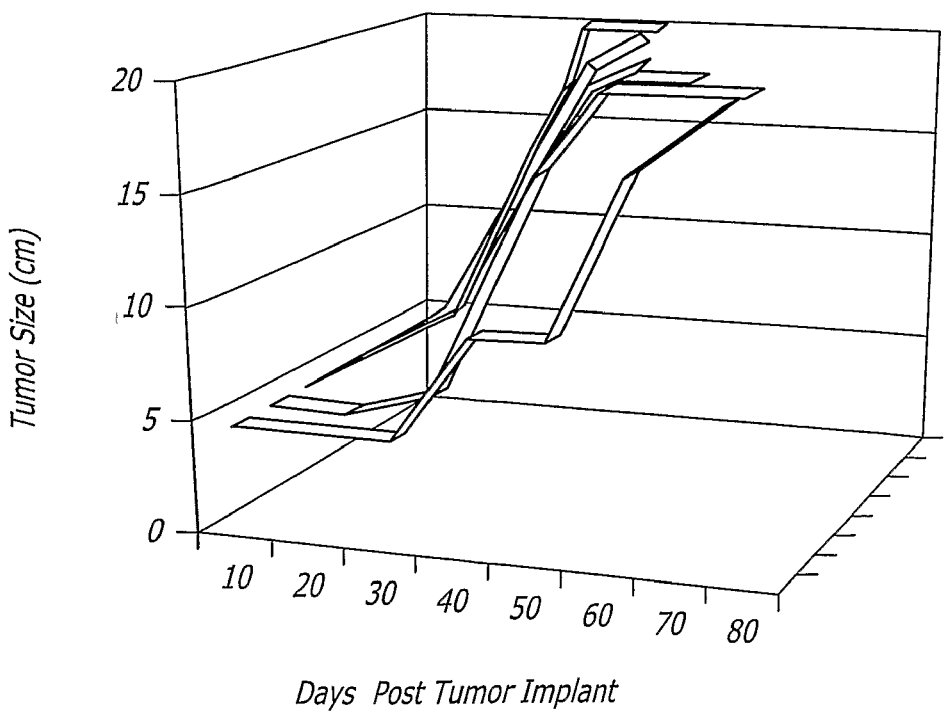

This highly conserved region of HIV-1 Tat is a canonical SH3 binding domain (FIG. 12).

The mouse hairless (hr) gene also has an SH3 binding motif of amino acids 176-196:

```
                                              (SEQ ID NO. 4)
Pro Cys Asp Trp Pro Leu Thr Pro Asp Pro Trp Val

Tyr Ser Gly Ser Gln Pro Lys Val Pro
```

Homology exists between the human Tat SH3 binding domain (SEQ ID NO. 3) and the SH3 binding domain of the mouse hr gene (SEQ ID NO. 4):

```
Human     3 Pro Val Arg Pro Asn Leu Glu Pro Trp Lys His Pro  14
Mouse   180 Pro Leu Thr Pro Asn --------Pro Trp Val Tyr Ser 189

Human    15 Gly Ser Gln Pro                                  18
Mouse   190 Gly Ser Gln Pro                                 193
```

Variants of Tat found in simian lentiviruses that do not cause immunodeficiency do not have an SH3 binding domain but instead have the following proline-flanked sequence:

```
                                              (SEQ ID NO. 5)
Pro Leu Arg Glu Gln Glu Asn Ser Leu Glu Ser Ser

Asn Glu Arg Ser Ser Cys Ile Leu Glu Ala Asp Ala

Thr Thr Pro
```

The human equivalent of the simian sequence above (SEQ ID NO. 5) is:

```
                                              (SEQ ID NO. 6)
    Ser Asn Glu Arg Ser Ser Cys Glu Leu Glu Val
```

Figure 10:
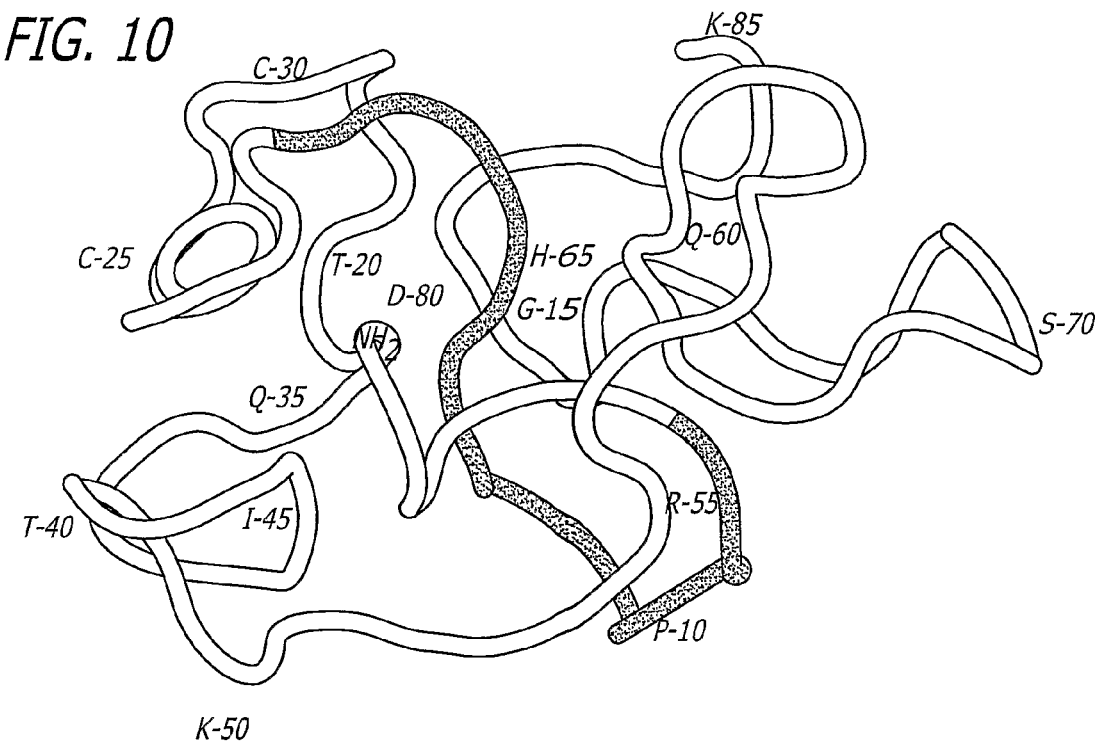
FIG. 10 depicts domain 1 of the Tat molecule, the signal transduction domain, amino acids 3-19 as indicated by the hatched portion of the molecule.

Another region of interest is a cysteine-rich proposed ligand binding domain (amino acids 22-37) which contains seven cysteines (FIG. 10).

```
                                              (SEQ ID No. 7)
Cys Thr Thr Cys Tyr Cys Lys Lys Cys Cys Phe His

Cys Gln Val Cys
```

Figure 11:
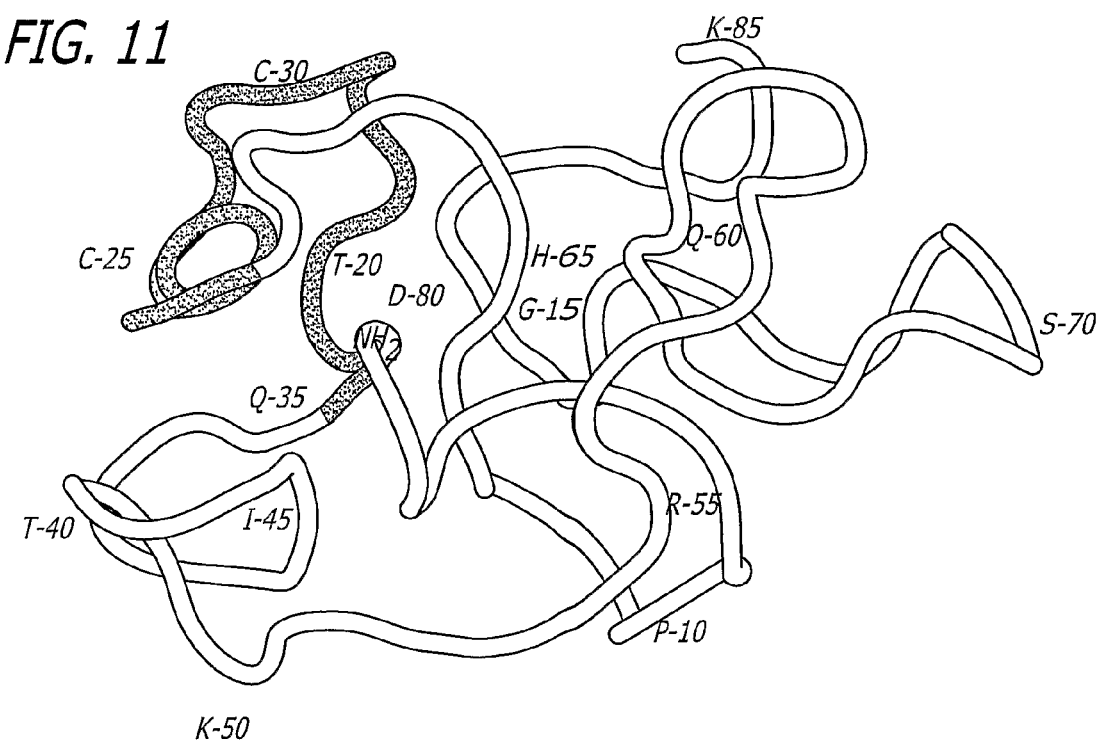
FIG. 11 depicts domain 2 of the Tat molecule, the cysteine-rich ligand binding domain, amino acids 22-37 as indicated by the hatched portion of the molecule.

Additionally, it is known that Tat contains a membrane translocation domain (MTS) (FIG. 11).

Example 5

In Vitro Bioassay for Monocyte Differentiation

The in vitro ultra-sensitive monocyte Tat bioassay of the present invention is used to assess the immunosuppressant or immunostimulatory activity of the Tat proteins used in tolerogen compositions of the present invention. This assay utilizes fresh monocyte cells substantially purified from human peripheral blood using standard density gradient enrichment procedures or other cell isolation protocols known in the art. The substantially purified monocytes are washed and then cultured in RPMI-1640 supplemented with 10% FBS at 37° C.

The in vitro ultra-sensitive monocyte Tat bioassay is performed using a positive control (FasL, inducing compound) and a negative control (no active compound is added to the culture). Suitable positive controls include, but are not limited to, lipopolysaccharide (LPS) and or tissue necrosing factor (TNF-α) at a final concentration of 100 ng/mL and 50 ng/mL, respectively. Test samples (Tat preparations) are run at final concentrations from 50 pM to 50 nM and include Tat, ox-Tat, NICE and other Tat derivatives and mutants.

The test samples and controls are individually mixed with the substantially pure monocytes seeded at a density of $10^6$ cells/mL in round bottom tubes containing RPMI-1640 with 10% FBS (herein referred to collectively as assay cultures). The assay cultures are then incubated for a suitable period of time, preferably from five to six days, at 37° C., in a 5% $CO_2$ environment.

At the end of the incubation period, cells are removed from each assay culture and the presence of any induced FasL expression (for measurement of differentiation into ARegs) or CD86 expression (for differentiation in dendritic cells) is detected by staining with an anti-FasL or anti-CD86 antibodies and appropriate fluorescent detection agents. After the substantially pure macrophages have been stained, the fluorescence is detected using a fluorescence activated cell sorter (FACS) system. Control staining is performed using the fluorescent detection system alone and subtracted from the specific anti-FasL or anti-CD86 staining seen in the assay cultures. The greater the percentage of FasL positive cells in a given assay culture, the more immunosuppressant the test sample in the assay culture is. Conversely, if the assay culture contains a predominance of CD86 positive cells, the test sample is identified to be immunostimulatory. Negative controls should always remain non-reactive with the antibodies and the positive control should fall within predetermined ranges.

Example 6 siRNA Targeting Domains

Human Tat SH3 targeting domain:

```
                                       (SEQ ID NO. 8)
ccagtagatc ctagactaga gccctggaag catccaggaa gtcagcctaa
```

Mouse Hairless SH3 targeting domain:

```
                                       (SEQ ID NO. 9)
ccatgtgact ggccctgac cccgcacccc tgggtatact ccgggggcca gcccaaagtg ccc
```

Targeting domain from the human equivalent of the simian non-immunosuppressive Tat motif:

```
                                      (SEQ ID NO. 10)
   agcaacgagc ggagttcctg cgagctagag gtg
```

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A method for identifying new immunomodulatory chemical entities (NICE) and characterizing the NICE as immunostimulatory or immunosuppressive comprising:
   a. reacting a candidate NICE with a Tat SH3 binding domain wherein said Tat SH3 binding domain is bound to a solid phase to identify candidate NICE that bind to said Tat SH3;
   b. identifying said candidate NICE bound to said Tat SH3;
   c. adding said identified candidate NICE to a culture of purified peripheral blood monocytes;
   d. adding Tat having an SH3 binding domain to said peripheral blood monocytes and candidate NICE to form a test culture;
   e. incubating said test culture to allow said monocytes to differentiate into dendritic cells (DC) or regulatory macrophages (AReg);
   f. removing said differentiated cells from said test culture;
   g. quantifying the numbers of DCs and AReg in the differentiated cell population; and
   h. determining the relative numbers of DCs and AReg in the differentiated cell population; wherein greater numbers of DCs compared to AReg identifies an immunosuppressive NICE and greater numbers of ARegs compared to DCs identifies an immunostimulatory NICE.

2. The method according to claim 1 wherein said Tat SH3 binding domain in step (a) is selected from the group consisting of native immunosuppressive human immunodeficiency virus (HIV) Tat, simian lentivirus Tat, long-term non-responder Tat, randomly mutated HIV Tat and site-specific mutated HIV Tat.

3. The method according to claim 1 further comprising the step of injecting an immunostimulatory NICE into an immunosuppressed mouse wherein said immunosuppression results from the presence of an endogenous SH3 binding domain and determining the numbers of ARegs in a sample of the mouse's peripheral blood before and after administration of the immunostimulatory NICE, wherein an increase in the number of ARegs confirms the NICE is immunostimulatory.

4. The method according to claim 3 wherein the said immunosuppressed mouse is a hairless (hr) mouse.

5. A method according to claim 1 further comprising the step of injecting an immunosuppressive NICE into a mouse and further challenging said mouse with an antigen wherein tolerance to said antigen confirms that the NICE is immunosuppressive.

* * * * *

SEQUENCE LISTING

<160> NUMBER OF SEQ ID NOS: 11

<210> SEQ ID NO 1
<211> LENGTH: 101
<212> TYPE: PRT
<213> ORGANISM: Human immunodeficiency virus type 1

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Cys Tyr Cys Lys Lys Cys Cys Phe
            20                  25                  30

His Cys Gln Val Cys Phe Thr Lys Lys Ala Leu Gly Ile Ser Tyr Gly
        35                  40                  45

Arg Lys Lys Arg Arg Gln Arg Arg Ala Pro Glu Asp Ser Gln Thr
    50                  55                  60

His Gln Val Ser Pro Lys Gln Pro Ala Pro Gln Phe Arg Gly Asp
65                  70                  75                  80

Pro Thr Gly Pro Lys Glu Ser Lys Lys Val Glu Arg Glu Thr Glu
                85                  90                  95

Thr His Pro Val Asp
            100

<210> SEQ ID NO 2
<211> LENGTH: 303
<212> TYPE: DNA
<213> ORGANISM: Human immunodeficiency virus type 1

<400> SEQUENCE: 2
atggagcccg tggaccctcg cctggagccc tggaagcacc cgggcagcca gcccaagacc      60
gcctgcacca catgttactg caagaagtgc tgcttccact gccaggtgtg cttcaccaag     120
aaggccttgg gcatcagcta cggccgcaag aagcgccggc agcgccgccg ggcccctgag     180
gacagccaga cccaccaggt gagccctccc aagcagcccg ctccacagtt ccgcggcgac     240
cctaccggtc ccaaggagag caagaagaag gtggagcgcg agaccgagac ccatcccgtc     300
gac                                                                   303

<210> SEQ ID NO 3
<211> LENGTH: 17
<212> TYPE: PRT
<213> ORGANISM: Human immunodeficiency virus type 1

<400> SEQUENCE: 3

Pro Val Asp Pro Arg Leu Glu Pro Trp Lys His Pro Gly Ser Gln Pro
1               5                   10                  15

Lys

<210> SEQ ID NO 4
<211> LENGTH: 21
<212> TYPE: PRT
<213> ORGANISM: Human immunodeficiency virus type 1

<400> SEQUENCE: 4

Pro Cys Asp Trp Pro Leu Thr Pro Asp Pro Trp Val Tyr Ser Gly Ser
1               5                   10                  15

Gln Pro Lys Val Pro
            20

-continued

```
<210> SEQ ID NO 5
<211> LENGTH: 27
<212> TYPE: PRT
<213> ORGANISM: Simian immunodeficiency virus

<400> SEQUENCE: 5

Pro Leu Arg Glu Gln Glu Asn Ser Leu Glu Ser Ser Asn Glu Arg Ser
1               5                   10                  15

Ser Cys Ile Leu Glu Ala Asp Ala Thr Thr Pro
            20                  25

<210> SEQ ID NO 6
<211> LENGTH: 11
<212> TYPE: PRT
<213> ORGANISM: Human immunodeficiency virus type 1

<400> SEQUENCE: 6

Ser Asn Glu Arg Ser Ser Cys Glu Leu Glu Val
1               5                   10

<210> SEQ ID NO 7
<211> LENGTH: 16
<212> TYPE: PRT
<213> ORGANISM: Human immunodeficiency virus type 1

<400> SEQUENCE: 7

Cys Thr Thr Cys Tyr Cys Lys Lys Cys Cys Phe His Cys Gln Val Cys
1               5                   10                  15

<210> SEQ ID NO 8
<211> LENGTH: 50
<212> TYPE: DNA
<213> ORGANISM: Human immunodeficiency virus type 1

<400> SEQUENCE: 8
ccagtagatc ctagactaga gccctggaag catccaggaa gtcagcctaa               50

<210> SEQ ID NO 9
<211> LENGTH: 63
<212> TYPE: DNA
<213> ORGANISM: Mus musculus

<400> SEQUENCE: 9
ccatgtgact ggcccctgac cccgcacccc tgggtatact ccggggggcca gcccaaagtg   60 ccc                                                                  63

<210> SEQ ID NO 10
<211> LENGTH: 33
<212> TYPE: DNA
<213> ORGANISM: Simian immunodeficiency virus

<400> SEQUENCE: 10
agcaacgagc ggagttcctg cgagttagag gtg                                 33

<210> SEQ ID NO 11
<211> LENGTH: 98
<212> TYPE: PRT
<213> ORGANISM: Artificial
<220> FEATURE:
<223> OTHER INFORMATION: Modified immunostimulatory Tat

<400> SEQUENCE: 11

Met Glu Pro Ser Asn Glu Arg Ser Ser Cys Glu Leu Glu Val Pro Lys
1               5                   10                  15
```

```
Thr Ala Cys Thr Thr Cys Tyr Cys Lys Lys Cys Cys Phe His Cys Gln
            20              25              30

Val Cys Phe Thr Lys Lys Ala Leu Gly Ile Ser Tyr Gly Arg Lys Lys
        35              40              45

Arg Arg Gln Arg Arg Ala Pro Glu Asp Ser Gln Thr His Gln Val
    50              55              60

Ser Pro Pro Lys Gln Pro Ala Pro Gln Phe Arg Gly Asp Pro Thr Gly
65              70              75              80

Pro Lys Glu Ser Lys Lys Lys Val Glu Arg Glu Thr Glu Thr His Pro
            85              90              95

Val Asp
```